US012346767B2

(12) United States Patent
Lynch

(10) Patent No.: US 12,346,767 B2
(45) Date of Patent: Jul. 1, 2025

(54) METHOD, APPARATUS AND WEARABLE ASSEMBLY

(71) Applicant: Prevayl Innovations Limited, Manchester (GB)

(72) Inventor: Michael John Lynch, Cheshire (GB)

(73) Assignee: Prevayl Innovations Limited, Wilmslow (GB)

( * ) Notice: Subject to any disclaimer, the term of this patent is extended or adjusted under 35 U.S.C. 154(b) by 18 days.

(21) Appl. No.: 17/999,972

(22) PCT Filed: Jun. 15, 2021

(86) PCT No.: PCT/GB2021/051489
§ 371 (c)(1),
(2) Date: Nov. 28, 2022

(87) PCT Pub. No.: WO2021/255430
PCT Pub. Date: Dec. 23, 2021

(65) Prior Publication Data
US 2023/0222302 A1    Jul. 13, 2023

(30) Foreign Application Priority Data

Jun. 17, 2020 (GB) .................................. 2009219
Sep. 10, 2020 (GB) .................................. 2014229

(51) Int. Cl.
*G06K 7/10* (2006.01)
*A61B 5/11* (2006.01)
(Continued)

(52) U.S. Cl.
CPC ........ *G06K 7/10396* (2013.01); *A61B 5/1118* (2013.01); *G06K 7/1417* (2013.01); *G06K 19/07762* (2013.01)

(58) Field of Classification Search
CPC ............. G06K 7/10396; G06K 7/1417; G06K 19/07762; G06K 19/0614; G06K 19/0716;
(Continued)

(56) References Cited

U.S. PATENT DOCUMENTS 9,554,721 B1    1/2017  Zikov
10,499,849 B1   12/2019 Chuang
(Continued)

FOREIGN PATENT DOCUMENTS

CN  204351118  5/2015
CN  206166913  5/2017
(Continued)

OTHER PUBLICATIONS

International Search Report received in PCT/GB2021/050284 mailed Apr. 12, 2021.
(Continued)

*Primary Examiner* — An T Nguyen
(74) *Attorney, Agent, or Firm* — Suzannah K. Sundby, Esq.; Canady + Lortz LLP

(57) ABSTRACT

The method comprises reading an electronics module identifier for an electronics module (S101); reading a wearable article identifier for a wearable article associated with the electronics module (S102); and associating the electronics module identifier with the wearable article identifier (S103).

22 Claims, 22 Drawing Sheets

(51) Int. Cl.
  *G06K 7/14* (2006.01)
  *G06K 19/077* (2006.01)
(58) Field of Classification Search
  CPC ... G06K 19/0723; A61B 5/1118; A61B 5/117;
                    A61B 5/6804; A41D 1/002
  See application file for complete search history.

(56) References Cited

U.S. PATENT DOCUMENTS

| | | |
|---|---|---|
| 2004/0171956 A1 | 9/2004 | Babashan |
| 2007/0208233 A1 | 9/2007 | Kovacs |
| 2008/0125288 A1 | 5/2008 | Case |
| 2008/0218310 A1 | 9/2008 | Alten |
| 2009/0030333 A1 | 1/2009 | McDonough |
| 2009/0069702 A1 | 3/2009 | How |
| 2009/0112072 A1 | 4/2009 | Banet |
| 2009/0192823 A1 | 7/2009 | Hawkins |
| 2010/0280331 A1 | 11/2010 | Kaufman |
| 2010/0292050 A1 | 11/2010 | Dibenedetto |
| 2010/0292599 A1 | 11/2010 | Oleson |
| 2011/0062237 A1 | 3/2011 | Chaves |
| 2012/0146784 A1 | 6/2012 | Hines |
| 2012/0235821 A1 | 9/2012 | DiBenedetto |
| 2012/0246795 A1 | 10/2012 | Scheffler |
| 2012/0306643 A1 | 12/2012 | Dugan |
| 2013/0120106 A1 | 5/2013 | Cauwels |
| 2013/0175334 A1 | 7/2013 | Miller |
| 2014/0040626 A1 | 2/2014 | Dan |
| 2014/0135644 A1 | 5/2014 | Kim |
| 2014/0221855 A1 | 8/2014 | McCaffrey |
| 2014/0275876 A1 | 9/2014 | Hansen |
| 2014/0288436 A1 | 9/2014 | Venkatraman |
| 2014/0318699 A1 | 10/2014 | Longinotti-Buitoni |
| 2014/0323827 A1 | 10/2014 | Ahmed |
| 2015/0061889 A1 | 3/2015 | Kotaki |
| 2015/0061891 A1 | 3/2015 | Oleson |
| 2015/0081169 A1 | 3/2015 | Pisz |
| 2015/0088002 A1 | 3/2015 | Podhajsky |
| 2015/0099991 A1 | 4/2015 | Yamaguchi |
| 2015/0170540 A1* | 6/2015 | Ford .................. G09B 9/003 434/22 |
| 2015/0182841 A1 | 7/2015 | Martikka |
| 2015/0230752 A1 | 8/2015 | Fort |
| 2015/0231481 A1 | 8/2015 | Jones |
| 2015/0305674 A1 | 10/2015 | McPherson |
| 2016/0058313 A1 | 3/2016 | Sato |
| 2016/0098581 A1 | 4/2016 | Santiago |
| 2016/0120460 A1 | 5/2016 | Eom |
| 2016/0134642 A1 | 5/2016 | Hamid |
| 2016/0135516 A1 | 5/2016 | Cobbett |
| 2016/0159106 A1 | 6/2016 | De Castro |
| 2016/0192716 A1 | 7/2016 | Lee |
| 2016/0256104 A1 | 9/2016 | Romem |
| 2016/0371438 A1 | 12/2016 | Annulis |
| 2016/0374588 A1 | 12/2016 | Shariff |
| 2017/0031435 A1 | 2/2017 | Raffle |
| 2017/0071548 A1 | 3/2017 | Wiebe |
| 2017/0086519 A1 | 3/2017 | Giancarlo |
| 2017/0094216 A1 | 3/2017 | Ekambaram |
| 2017/0140120 A1 | 5/2017 | Thrower |
| 2017/0181703 A1 | 6/2017 | Kaib |
| 2017/0196513 A1 | 7/2017 | Longinotti-Buitoni |
| 2017/0243615 A1 | 8/2017 | Tabak |
| 2017/0303864 A1 | 10/2017 | Su |
| 2017/0332946 A1 | 11/2017 | Kikkeri |
| 2017/0368413 A1 | 12/2017 | Shavit |
| 2018/0092698 A1 | 4/2018 | Chopra |
| 2018/0174683 A1 | 6/2018 | Franz |
| 2018/0218187 A1* | 8/2018 | Freeman .................. G06F 21/45 |
| 2018/0228406 A1 | 8/2018 | Mendelsohn |
| 2018/0232925 A1 | 8/2018 | Frakes |
| 2018/0300919 A1 | 10/2018 | Muhsin |
| 2018/0345079 A1 | 12/2018 | Lindman |
| 2018/0353152 A1 | 12/2018 | Teji |
| 2018/0358119 A1 | 12/2018 | Bhushan |
| 2019/0000384 A1 | 1/2019 | Gupta |
| 2019/0037932 A1 | 2/2019 | Martin |
| 2019/0053469 A1 | 2/2019 | Mardirossian |
| 2019/0090765 A1 | 3/2019 | Cuccinello |
| 2019/0196411 A1 | 6/2019 | Yuen |
| 2019/0246734 A1 | 8/2019 | Nurse |
| 2020/0333837 A1 | 10/2020 | Weiner |
| 2020/0367758 A1 | 11/2020 | Kimura |
| 2022/0101994 A1 | 3/2022 | Crofts |
| 2022/0142572 A1 | 5/2022 | Crofts |
| 2023/0115286 A1 | 4/2023 | Crofts |

FOREIGN PATENT DOCUMENTS

| | | |
|---|---|---|
| CN | 208624750 | 3/2019 |
| CN | 110584627 | 12/2019 |
| CN | 209928492 | 1/2020 |
| CN | 111035376 | 4/2020 |
| EP | 3431146 | 1/2019 |
| GB | 2476690 | 7/2011 |
| GB | 2561575 | 10/2018 |
| GB | 2563065 | 12/2018 |
| GB | 2565330 | 2/2019 |
| GB | 2567533 | 4/2019 |
| GB | 2586950 | 3/2021 |
| GB | 2590986 | 7/2021 |
| GB | 2591819 | 8/2021 |
| GB | 2593433 | 9/2021 |
| GB | 2593434 | 9/2021 |
| GB | 2596157 | 12/2021 |
| GB | 2596158 | 12/2021 |
| GB | 2596782 | 1/2022 |
| GB | 2596783 | 1/2022 |
| GB | 2590985 | 4/2022 |
| JP | 2015073807 | 4/2015 |
| KR | 101907383 | 10/2018 |
| WO | 0004522 | 1/2000 |
| WO | 2006009830 | 1/2006 |
| WO | 2008038141 | 4/2008 |
| WO | 2012167026 | 12/2012 |
| WO | 2014192002 | 12/2014 |
| WO | 2015056262 | 4/2015 |
| WO | 2017198978 | 11/2017 |
| WO | 2018134432 | 7/2018 |
| WO | 2018145719 | 8/2018 |
| WO | 2018152475 | 8/2018 |
| WO | 2019086908 | 5/2019 |
| WO | 2019104374 | 6/2019 |

OTHER PUBLICATIONS

Written Opinion received in PCT/GB2021/050284 mailed Apr. 12, 2021.
"EMGlare Heart", available from https://emglare.com/ by at least Aug. 20, 2021, , Publisher: emglare.com [online].
"Enflux Exercise Clothing: Improve Form! Real-time Analysis", https://www.kickstarter.com/projects/1850884998/enflux-smart-clothing-3d-workout-tracking-and-form/description, Mar. 1, 2017, Publisher: Enflux exercise clothing, kickstarter.com, [online].
Examination Report received in GB1908181.9 mailed Mar. 16, 2020.
Examination Report received in GB1908181.9 mailed Apr. 16, 2021.
Search Report received in GB1908181.9 mailed Dec. 9, 2019.
Examination Report received in GB1908187.6 mailed May 29, 2020.
Search and Examination Report received in GB1908187.6 mailed Dec. 12, 2019.
Prosecution history of GB2590985, granted Mar. 15, 2022.
Lightbody et al., A versatile high-performance visual fiducial marker detection system with scalable identity encoding, Apr. 3, 2017, pp. 276-282, Publisher: Proceedings of the Symposium on Applied Computing.
Https://nakedlabs.com/naked-home-body-scanner, , Publisher: Naked Labs available at least by Oct. 4, 2018.

(56) References Cited

OTHER PUBLICATIONS

"QR Code & Bluetooth Connection Tutorial with Shimmer", https://www.youtube.com/watch?v=l6pZLr2h9ag, , Page(s) (screenshot provided), Publisher: YouTube video purportedly uploaded by Shimmer Sensing on Feb. 6, 2014.
Prosecution in U.S. Appl. No. 17/432,583.
Prosecution in U.S. Appl. No. 17/432,586.
Prosecution in U.S. Appl. No. 17/796,845.
Prosecution in U.S. Appl. No. 18/081,016.
International Search Report received in PCT/GB2020/051360 mailed Aug. 20, 2020.
Written Opinion received in PCT/GB2020/051360 mailed Aug. 20, 2020.
International Search Report received in PCT/GB2020/051361 mailed Aug. 4, 2020.
Written Opinion received in PCT/GB2020/051361 mailed Aug. 4, 2020.
International Search Report received in PCT/GB2021/051489 mailed Sep. 20, 2021.
Written Opinion received in PCT/GB2021/051489 mailed Sep. 20, 2021.

* cited by examiner

METHOD, APPARATUS AND WEARABLE ASSEMBLY

The present invention is directed towards a method, apparatus and wearable assembly as set out in the accompanying claims.

BACKGROUND

Wearable articles can be designed to interface with a user of the article, and to determine information such as the user's heart rate, rate of respiration, activity level, and body positioning. The articles include electrically conductive pathways to allow for signal transmission between an electronics module for processing and communication and sensing components of the article. The wearable articles may be garments. Such garments are commonly referred to as 'smart clothing' and may also be referred to as 'biosensing garments' if they measure biosignals.

It is desirable to overcome at least some of the problems associated with the prior art, whether explicitly discussed herein or otherwise.

SUMMARY

According to the present disclosure there is provided a wearable assembly, apparatus and method as set forth in the appended claims. Other features of the invention will be apparent from the dependent claims, and the description which follows.

According to a first aspect of the disclosure, there is provided a method. The method comprises reading an electronics module identifier for an electronics module. The method comprises reading a wearable article identifier for a wearable article associated with the electronics module. The method comprises associating the electronics module identifier with the wearable article identifier.

Reading the electronics module identifier may comprise communicating with the electronics module. The communication may be over a wireless communication protocol. Reading the electronics module identifier may comprise triggering the electronics module to transmit the electronics module identifier over the wireless communication protocol. Triggering the electronics module may comprise energizing the electronics module to transmit the electronics module identifier.

Reading the wearable article identifier may comprise reading a machine-readable code of the wearable article. Reading the machine-readable code may comprise capturing an image of the machine-readable code.

The method may further comprise obtaining activity data and an electronics module identifier from an electronics module. The method may further comprise identifying the user wearing the electronics module by identifying the wearable article identifier associated with the electronics module identifier. The method may further comprise displaying the activity data, optionally along with identifying information for the user.

The method may further comprise obtaining activity data and electronics module identifiers from a plurality of electronics modules. The method may further comprise for at least one of the electronics modules, identifying the user wearing the electronics module by identifying the wearable article identifier associated with the received electronics module identifier for the wearable article. The method may further comprise for a plurality of the electronic modules, identifying the user wearing the electronics module by identifying the wearable article identifier associated with the received electronics module identifier for the wearable article. The method may further comprise displaying the activity data for the plurality of electronics modules along with identifying information for the users associated with the plurality of electronics modules.

The method may further comprise obtaining a wearable article identifier for a wearable article. The method may further comprise using the wearable article identifier to identify an electronics module identifier associated with the wearable article identifier. The method may further comprise using the electronics module identifier to obtain activity data for the user wearing the wearable article from the electronics module.

The method may comprise displaying the activity data along with identifying information for the user.

The method may further comprise obtaining wearable article identifiers for a plurality of wearable articles. The method may comprise, for at least one of the wearable article identifiers: identifying an electronics module identifier associated with the wearable article identifier. The method may further comprise using the electronics module identifier to obtain activity data for the user wearing the wearable article from the electronics module.

The method may further comprise for a plurality of the wearable article identifiers: identifying an electronics module identifier associated with the wearable article identifier. The method may further comprise using the electronics module identifier to obtain activity data for the user wearing the wearable article from the electronics module. The method may further comprise displaying the activity data for the plurality of electronic modules along with identifying information for the users associated with the plurality of electronic modules.

Using the identified electronics module identifier to obtain activity data from the electronics module may comprise: receiving activity data and an electronics module identifier from an electronics module; and may comprise determining that the received electronics module identifier matches the identified electronics module identifier. The activity data and the electronics module identifier may be received indirectly from the electronics module via an external apparatus.

Using the electronics module identifier to obtain activity data from for the user wearing the wearable article from the electronics module may comprise transmitting the electronics module identifier to an external apparatus and may comprise receiving, from the external apparatus, activity data from the electronics module.

The method may comprise transmitting the associated electronics module identifier and the wearable article identifier to an external apparatus.

The step of reading a wearable article identifier for a wearable article may comprise reading a non-visible wearable article identifier for a wearable article associated with the electronics module; and the step of associating the electronics module identifier with the wearable article identifier may comprise associating the electronics module identifier with the non-visible wearable article identifier.

According to a second aspect of the disclosure, there is provided a computer program comprising instructions which, when executed by a computer apparatus, cause the computer apparatus to perform the method of the first aspect of the disclosure.

According to a third aspect of the disclosure, there is provided an apparatus. The apparatus comprises a first reader arranged to read an electronics module identifier for an electronics module. The apparatus comprises a second reader arranged to read a wearable article identifier for a wearable article associated with the electronics module. The apparatus comprises a controller operable to associate the electronics module identifier with the wearable article identifier.

The apparatus may comprise a display arranged to display the received activity data.

The first reader may comprise a communicator arranged to communicate with the electronics module.

The first reader may comprise a wireless communicator arranged to communicate with the electronics module over a wireless communication protocol.

The second reader may comprise a camera arranged to obtain an image of the wearable article identifier.

According to a fourth aspect of the disclosure, there is provided a method. The method comprises obtaining a wearable article identifier for a wearable article. The method comprises using the wearable article identifier to identify an electronics module identifier for an electronics module associated with the wearable article identifier. The method comprises using the electronics module identifier to obtain activity data for the user wearing the wearable article from the electronics module.

Obtaining the wearable article identifier may comprise receiving the wearable article identifier from an external apparatus.

Obtaining the wearable article identifier may comprise reading the wearable article identifier from the wearable article. Reading the wearable article identifier may comprise reading a machine-readable code of the wearable article. Reading the machine-readable code may comprises capturing an image of the machine-readable code.

Using the identified electronics module identifier to obtain activity data may comprise receiving activity data and an electronics module identifier from an electronics module and determining that the received electronics module identifier matches the identified electronics module identifier. The activity data and the electronics module identifier may be received indirectly from the electronics module via an external apparatus or may be directly received from the electronics module.

Using the electronics module identifier to obtain activity data may comprise transmitting the electronics module identifier to an external apparatus and receiving, from the external apparatus, activity data from the electronics module.

The method may further comprise displaying the activity data. The method may further comprise displaying identifying information for the user along with the activity data. The method may further comprise simultaneously displaying a representation of the user wearing the wearable article and the activity data, optionally wherein the representation of the user is a live view image of the user.

The method may further comprise obtaining wearable article identifiers for a plurality of wearable articles. The method may further comprise, for at least one of the wearable article identifiers: identifying an electronics module identifier for an electronics module associated with the wearable article identifier; and may further comprise using the electronics module identifier to obtain activity data for the user wearing the wearable article from the electronics module.

The method may further comprise, for a plurality of the wearable article identifiers: identifying an electronics module identifier for an electronics module associated with the wearable article identifier; and may further comprise using the electronics module identifier to obtain activity data for the user wearing the wearable article from the electronics module.

The method may further comprise displaying the activity data for the plurality of electronic modules along with identifying information for the users associated with the plurality of electronic modules.

The method may further comprise reading an electronics module identifier for an electronics module. The method may further comprise reading a wearable article identifier for a wearable article associated with the electronics module. The method may further comprise associating the electronics module identifier with the wearable article identifier.

Reading the electronics module identifier may comprise communicating with the electronics module. The communication may be over a wireless communication protocol. Reading the electronics module identifier may comprise triggering the electronics module to transmit the electronics module identifier over the wireless communication protocol.

The method may further comprise obtaining activity data and an electronics module identifier from an electronics module. The method may further comprise identifying the user wearing the electronics module by identifying the wearable article identifier associated with the electronics module identifier.

The method may comprise obtaining activity data and electronics module identifiers from a plurality of electronics modules. The method may comprise, for at least one of the electronics modules, identifying the user wearing the electronics module by identifying the wearable article identifier associated with the received electronics module identifier for the wearable article.

The method may further comprise, for a plurality of the electronic modules, identifying the user wearing the electronics module by identifying the wearable article identifier associated with the received electronics module identifier for the wearable article.

The method may further comprise displaying the activity data for the plurality of electronics modules along with identifying information for the users associated with the plurality of electronics modules.

The method may further comprise transmitting the associated electronics module identifier and the wearable article identifier to an external apparatus.

According to a fifth aspect of the disclosure, there is provided a computer program comprising instructions which, when executed by a computer apparatus, cause the computer apparatus to perform the method of the fourth aspect of the disclosure.

According to a sixth aspect of the disclosure, there is provided an apparatus comprising a controller operable to: obtain a wearable article identifier for a wearable article; use the wearable article identifier to identify an electronics module identifier for an electronics module associated with the wearable article identifier; and use the electronics module identifier to obtain activity data for the user wearing the wearable article from the electronics module.

According to a seventh aspect of the disclosure, there is provided a wearable assembly. The wearable assembly comprises an electronics module. The electronics module comprises a controller arranged to interface with a sensing component so as to receive activity data associated with a user wearing the wearable assembly. The electronics module comprises a communicator arranged to communicate an electronics module identifier to an external apparatus over a wireless communication protocol. The wearable assembly further comprises a wearable article comprising a wearable article identifier.

The wearable article identifier may comprise a machine-readable code.

The wearable article identifier may be readable from an outside surface of the wearable article.

The electronics module may be releasably attached to the wearable article.

The electronics module may be separate from the wearable article.

The communicator may be arranged to transmit the electronics module identifier to the external apparatus.

The communicator may be arranged to transmit the electronics module identifier to the external apparatus in response to the external apparatus being brought into proximity with the electronics module.

The electronics module may further comprise a sensor. The sensor may be arranged to detect the external apparatus being brought into proximity with the electronics module.

The sensor may be a motion sensor. The motion sensor may be arranged to detect a displacement of the electronics module caused by the external apparatus being brought into proximity with the electronics module.

In response to the sensor detecting the external apparatus being brought into proximity with the electronics module, the controller may be arranged to energize the communicator to transmit the electronics module identifier to the mobile device over the wireless communication protocol.

In response to the sensor detecting the external apparatus being brought into proximity with the electronics module, the controller may be arranged to transition from a low power mode to a normal power mode.

The wearable article identifier may be provided on an outside surface of the wearable article.

The wearable article identifier may be provided in a visual symbol.

The visual symbol may be a fiducial marker.

Beneficially, a fiducial marker is useable as a point of reference for the wearable article and thus enables the position of the wearable article and the motion of the wearable article over time to be monitored simply by capturing images of the wearable article. In this way, the motion of the user of the wearable article is tracked by determining the location of the fiducial marker in the captured image. The fiducial marker may be in the form of a 2D image. The fiducial is simple, of low cost and does not negatively affect the comfort of the wearable article for the user. The fiducial marker may be an augmented reality (AR) marker.

The wearable article identifier may have a limited visual footprint on the wearable article. This means that the wearable article identifier may be sufficiently small that it is not easily visible by the naked eye but is still machine-readable. The wearable article identifier may be non-visible or hidden within or behind the wearable article while still being readable from the outside surface of the wearable article. The wearable article identifier may be in the form of an NFC/RFID tag incorporated into the wearable article or other forms of non-visible marker as described below in relation to the eighth to twelfth aspects of the disclosure.

The wearable article may comprise a plurality of machine-readable codes. The machine-readable codes may each comprise the wearable article identifier and may comprise additional information.

The wearable article identifier may be integrated into the wearable article. The wearable article identifier may be printed onto or into the wearable article. Any known printing technique may be used such as screen printing or inkjet printing.

The wearable article identifier may be incorporated into or form part of visual element on the wearable article which may be a decorative item in the wearable article. The decorative item may be a logo, design, image, motif or pattern on the wearable article. In this way, the wearable article identifier may contribute to or enhance the appearance of the wearable article.

The wearable article may be a garment.

The electronics module may be releasably attached to a garment.

According to an eighth aspect of the present invention, there is provided a method comprising: reading an electronics module identifier for an electronics module; reading a non-visible wearable article identifier for a wearable article associated with the electronics module; and associating the electronics module identifier with the non-visible wearable article identifier.

The method may comprise obtaining activity data and an electronics module identifier from the electronics module, obtaining a non-visible wearable article identifier of the at least one wearable article, identifying the electronics module identifier associated with the obtained non-visible wearable article identifier, accessing the activity data obtained from the identified electronics module and displaying the obtained activity data in accordance with the associated non-visible wearable article identifier.

Obtaining the non-visible wearable article identifier may comprise scanning the non-visible wearable article identifier with a capturing device configured to read a non-visible machine-readable code of the wearable article.

Reading the non-visible wearable article identifier may comprise scanning the non-visible wearable article identifier with a capturing device configured to read a non-visible machine-readable code of the wearable article.

Scanning the non-visible wearable article identifier with a capturing device may comprise transmitting a non-visible signal onto the non-visible wearable article identifier, detecting any returned non-visible signal reflected from the non-visible wearable article identifier and determining the non-visible machine-readable code of the wearable article from the returned non-visible signal.

The non-visible signal may be an infra-red signal.

The activity data may be displayed along with identifying information for the wearer.

The method may further comprise reading at least one secondary display marker on the wearable article and displaying the activity data in accordance with the at least one secondary marker.

The method may further comprise: reading an electronics module identifier for a plurality of electronics modules; reading a non-visible wearable article identifier for a plurality of wearable articles associated with the plurality of electronics modules; associating each electronics module identifier with a respective the non-visible wearable article identifier; obtaining activity data and an electronics module identifier from the plurality of electronics modules; obtaining a non-visible wearable article identifier from at least one of the plurality of wearable articles; identifying an electronics module identifier associated with the at least one of the plurality of wearable article identifiers; accessing the activity data obtained with the identified electronics module identifier; and displaying the obtained activity data in accordance with the associated non-visible wearable article identifier.

The method may further comprise displaying the activity data obtained with the identified electronics module identifier along with identifying information for the wearer of the at least one of the plurality of wearable articles.

The activity data and the electronics module identifier may be received indirectly from the electronics module via an external apparatus.

Obtaining the electronics module identifier may comprise transmitting the electronics module identifier to an external apparatus and receiving, from the external apparatus, activity data from the electronics module.

According to a ninth aspect of the present invention, there is provided a computer program, the computer program comprising instructions which, when executed by a computer apparatus, cause the computer apparatus to perform the method of the eighth aspect of the present disclosure.

According to a tenth aspect of the present invention, there is provided an apparatus, the apparatus comprises a first reader arranged to read an electronics module identifier for an electronics module, a second reader arranged to read a non-visible wearable article identifier for a wearable article associated with the electronics module and a controller operable to associate the electronics module identifier with the wearable article identifier.

The first reader may comprise a wireless communicator arranged to communicate with the electronics module over a wireless communication protocol.

The second reader may comprise a capturing device arranged to read a non-visible machine-readable code of the wearable article.

The capturing device may be a sensor configured to transmit a non-visible signal onto the non-visible wearable article identifier. The capturing device may be configured to detect any received non-visible signal reflected from the non-visible wearable article identifier and the controller may be configured to determine the non-visible machine-readable code.

The sensor may be an infra-red sensor and the non-visible signal may be an infra-red signal.

The apparatus may further comprise a display and the controller may be configured to: obtain activity data and an electronics module identifier from the first reader and to obtain a non-visible wearable article identifier from a wearable article; identify the electronics module identifier associated with the obtained non-visible wearable article identifier, access the activity data obtained from the identified electronics module; and display the obtained activity data on the display in accordance with the associated non-visible wearable article identifier.

According to an eleventh aspect of the present invention, there is provided a wearable article comprising a body portion, the wearable article having a non-visible wearable article identifier provided thereon.

The body portion may include an inner surface and an outer surface, and the non-visible wearable article identifier is provided on the inner surface of the wearable article.

The body portion may include an inner surface and an outer surface, and the non-visible wearable article identifier is provided on the outer surface of the wearable article.

At least a portion of the body portion may comprise an outer layer and an inner layer, and wherein the non-visible wearable article identifier is provided between the inner and the outer layer.

The non-visible wearable article identifier may be provided on the inner layer. Alternatively, the non-visible wearable article identifier may be integral with the inner layer, or the non-visible wearable article identifier may be provided on the outer layer.

The non-visible wearable article identifier may be provided over a substantial part of the body portion of the wearable article The non-visible wearable article identifier may comprise a machine-readable code identifying the wearable article.

The non-visible wearable article identifier may be arranged to have spatially-varying properties that are configured to define the machine-readable code.

The non-visible wearable article identifier may comprise an arrangement of infrared absorbing regions and infrared non-absorbing regions arranged and configured to encode information therein to define the machine-readable code.

The non-visible wearable article identifier may be a fiducial marker.

The wearable article may include at least one secondary fiducial marker in addition to the non-visible wearable article identifier.

The wearable article may be a garment.

According to a twelfth aspect of the present invention, there is provided a wearable assembly comprising an electronics module comprising a controller arranged to interface with a sensing component so as to receive activity data associated with a wearer wearing the wearable assembly, and a communicator arranged to communicate an electronics module identifier to an external apparatus over a wireless communication protocol and a wearable article according to the tenth aspect of the present invention.

The electronics module may be releasably attached to the wearable article.

The electronics module may be separate from the wearable article.

The present invention has the advantage of an improved wearable assembly, apparatus and method. The wearable article of the wearable assembly uses a wearable article identifier, particularly a non-visible wearable article identifier, which can be read at a greater distance so is particularly applicable to scenarios in which the wearer of the wearable article is further away, for example on a football pitch. With a non-visible wearable article identifier, it can be provided over a greater portion of the wearable article which enables the identifier more easily readable. It also enables a greater portion of the wearable article to include additional markings such as sponsor details, players' names and the like.

BRIEF DESCRIPTION OF THE DRAWINGS

Examples of the present disclosure will now be described with reference to the accompanying drawings, in which.

DETAILED DESCRIPTION

Figure 1:
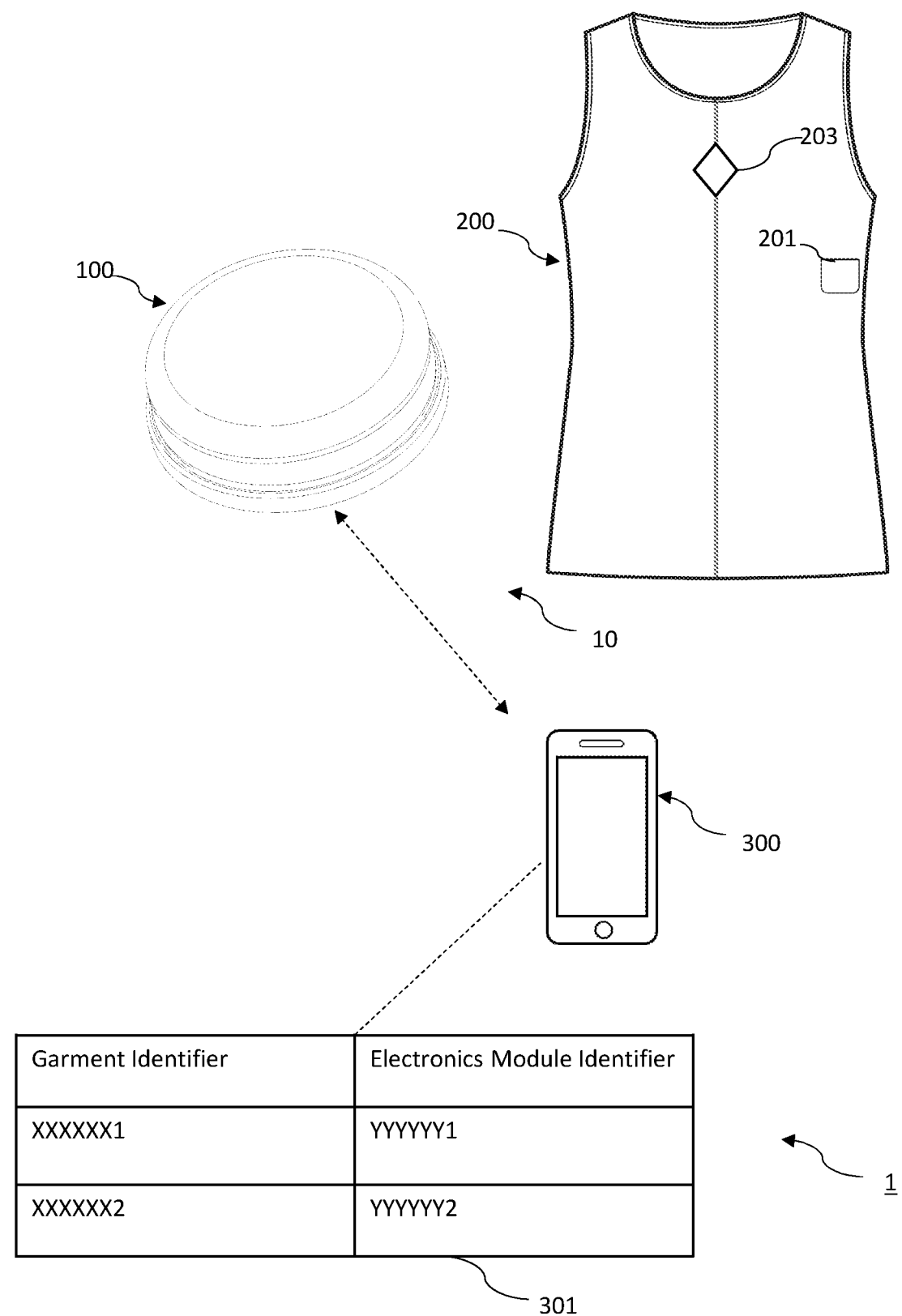
FIG. 1 shows a schematic diagram of an example system according to aspects of the present disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise.

"Wearable article" as referred to throughout the present disclosure may refer to any form of article which may be worn by a user such as a smart watch, necklace, bracelet, or glasses. The wearable article may be a textile article. The wearable article may be a garment. The garment may refer to an item of clothing or apparel. The garment may be a top. The top may be a shirt, t-shirt, blouse, sweater, jacket/coat, or vest. The garment may be a dress, brassiere, shorts, pants, arm or leg sleeve, vest, jacket/coat, glove, armband, underwear, headband, hat/cap, collar, wristband, stocking, sock, or shoe, athletic clothing, personal protecting equipment, swimwear, wetsuit or drysuit The garment may be a tight-fitting garment. Beneficially, a tight-fitting garment helps ensure that the sensor devices of the garment are held in contact with or in the proximity of a skin surface of the user. The garment may be a compression garment. The garment may be an athletic garment such as an elastomeric athletic garment.

The wearable article may be constructed from a woven or a non-woven material. The wearable article may be constructed from natural fibres, synthetic fibres, or a natural fibre blended with one or more other materials which can be natural or synthetic. The yarn may be cotton. The cotton may be blended with polyester and/or viscose and/or polyamide according to the application. Silk may also be used as the natural fibre. Cellulose, wool, hemp and jute are also natural fibres that may be used in the wearable article. Polyester, polycotton, nylon and viscose are synthetic fibres that may be used in the wearable article.

The garment comprises a sensing component or more typically a plurality of sensing components. The activity data obtained by the sensing components is transmitted by an electronic module of the garment to a server or external device. The electronic module may be in the form of a detachable electronic device that can be inserted into, for example, a pocket of the garment. The activity data may comprise any or a combination of the different example measurements described above.

The garment may be worn by a first person referred to as the "wearer". A second person referred to as the "user" is in possession of a user electronic device such as a mobile phone. The second person may desire to see activity data for the wearer as recorded by the sensors of the garment. For example, the user may be a sports coach that may desire to view metrics such as the wearer's heartrate, respiration levels and hydration levels of the wearer. The user may also be a healthcare professional such as a physiotherapist or doctor.

In some examples, the "user" and the "wearer" refer to the same person.

According to aspects of the present invention, a garment is provided having a marker located on the garment. The garment may be provided with a plurality of markers Preferably, the marker is a fiducial marker. Fiducial markers can be used as part of an augmented reality (AR) application, for example to provide an easily visible display of activity data which can be displayed or overlaid over an image of a wearer of the garment as taken by an imaging device, for example a camera housed within an electronic device such as a mobile phone, and operated by a user, or by one of more remote cameras located within the wearer's environment.

Augmented reality (AR) markers are cues which trigger the display of the virtual information. The clues may be visual clues. Markers are trained beforehand so that they can be recognized later in the camera stream. After an AR marker is recognized, its position, scale, and rotation are derived from visual cues and transferred to the virtual information.

In the present exemplar application, a sports coach can simply take a video of a sports person during activity at a remote distance and display the activity data within the video image showing on their mobile phone.

The following description refers to examples of the present disclosure where the wearable article is a garment. It will be appreciated that the present disclosure is not limited to garments and other forms of wearable article are within the scope of the present disclosure as outlined above.

Referring to FIG. 1, there is shown an example system 1 according to aspects of the present disclosure. The system 1 comprises wearable assembly 10 and apparatus 300 in the form of a mobile device 300. The wearable assembly 10 comprises an electronics module 100, and a garment 200.

The electronics module 100 is arranged to wirelessly communicate data to the mobile device 300. Various protocols enable wireless communication between the electronics module 100 and the mobile device 300. Example communication protocols include Bluetooth®, Bluetooth® Low Energy, and near-field communication (NFC).

The garment 200 has sensing components provided on an inside surface which are held near a skin surface of a wearer wearing the wearable assembly 10. This enables the sensing components to measure activity data such as biosignals for the wearer wearing the garment 200.

The sensing components may be arranged to sense one or more signals external to the wearer.

The sensing components may comprise any or a combination of a temperature sensor, a camera, a location tracking module such as a GPS module, and a chemical sensor.

The sensing components may be arranged to measure one or more biosignals of a wearer wearing the wearable article. Here, "biosignal" may refer to any signal in a living being that can be measured and monitored. The term "biosignal" is not limited to electrical signals and can refer to other forms of non-electrical biosignals. The sensing components may be used for measuring one or a combination of bioelectrical, bioimpedance, biochemical, biomechanical, bioacoustics, biooptical or biothermal signals of the wearer. The bioelectrical measurements include electrocardiograms (ECG), electrogastrograms (EGG), electroencephalograms (EEG), and electromyography (EMG). The bioimpedance measurements include plethysmography (e.g., for respiration), body composition (e.g., hydration, fat, etc.), and electroimpedance tomography (EIT). The biomagnetic measurements include magnetoneurograms (MNG), magnetoencephalography (MEG), magnetogastrogram (MGG), magnetocardiogram (MCG).

The biochemical measurements include glucose/lactose measurements which may be performed using chemical analysis of the user's sweat. The biomechanical measurements include blood pressure. The bioacoustics measurements include phonocardiograms (PCG). The biooptical measurements include orthopantomogram (OPG). The biothermal measurements include skin temperature and core body temperature measurements. The sensing components may comprise a radar unit. The wearable article may sense a combination of external signals and biosignals of the user.

The activity data may comprise any or a combination of the different example measurements described above.

The garment 200 has an electronics module holder 201 in the form of a pocket 201. The pocket 201 is sized to receive the electronics module 100. When disposed in the pocket 201, the electronics module 100 is arranged to integrate with the sensing components of garment 200 and receive activity data from the sensing components. The electronics module 100 is therefore removable from the garment 200.

The present disclosure is not limited to electronics module holders 201 in the form pockets 201. Instead, other mechanism for releasably mechanically coupling the electronics module 100 to the garment 200 may be provided. The mechanical coupling of the electronic module 100 to the garment 200 may be provided by a mechanical interface such as a clip, a plug and socket arrangement, etc. The mechanical coupling or mechanical interface may be configured to maintain the electronic module 100 in a particular orientation with respect to the garment 200 when the electronic module 100 is coupled to the garment 200. This may be beneficial in ensuring that the electronic module 100 is securely held in place with respect to the garment 200 and/or that any electronic coupling of the electronic module 100 and the garment 200 (or a component of the garment 200) can be optimized. The mechanical coupling may be maintained using friction or using a positively engaging mechanism, for example.

Beneficially, the removable electronic module 100 may contain all the components required for data transmission and processing such that the garment 200 only comprises the sensing components and communication pathways. In this way, manufacture of the garment 200 may be simplified. In addition, it may be easier to clean a garment 200 which has fewer electronic components attached thereto or incorporated therein. Furthermore, the removable electronic module 100 may be easier to maintain and/or troubleshoot than embedded electronics. The electronic module 100 may comprise flexible electronics such as a flexible printed circuit (FPC). The electronic module 100 may be configured to be electrically coupled to the garment 200.

The electronics module 100 transmits the activity data to an external apparatus such as mobile device 300.

In environments such as team sports or workplace settings, there may be a number of different wearers wearing different wearable assemblies 10 at the same time. Each of the wearable assemblies 10 will have a different electronics module 100 transmitting data to the same external apparatus such as mobile device 300. The data transmitted by the electronics module 100 will be associated with an electronics module identifier that uniquely identifies the electronics module 100. The electronics module identifier may be, for example, a communication address for the electronics module 100.

Generally, it is desirable that there is no fixed association between electronics module 100 and a garment. This provides greater flexibility in a sports or workplace setting. A pool of electronics modules 100 may be maintained by a central provider. This enables one electronics module 100 to be, over time, used with different garments 200 worn by different individuals. Because there is no fixed association between a wearer of a garment 200 and a particular electronics module 100 incorporated into the pocket 201 of the garment 200, it will be challenging and may not be possible (depending on the number of electronics modules, for example) for the mobile device 300 to confidently determine which garment, and thus which wearer, the received activity data relates to. This limits the utility of the received activity data as it is not possible to provide insights and analysis for a particular wearer.

To overcome this problem, the garment 200 of the wearable assembly 10 includes a wearable article identifier 203. The wearable article identifier 203 is a machine-readable code that is readable from the outside surface of the garment 200. The wearable article identifier 203 identifies the garment 200, and thus the wearer. The electronics module identifier is different to the wearable article identifier 203 and identifies the electronics module 100 which has no fixed association with the garment 200.

In an example operation, the mobile device 300 communicates with the electronics module 100 to obtain the electronics module identifier for the electronics module 100. The mobile device 300 also reads the machine-readable code 203 of the garment 200 to obtain the wearable article identifier 203 for the garment 200. The mobile device 300 then associates the electronics module identifier with the wearable article identifier 203. In this way, when activity data is received from the electronics module 100, the mobile device 300 is able to determine that the activity data relates to a particular garment 200 and thus a particular wearer.

In a preferred implementation, the association between the electronics module 100 and the garment 200 is formed once the electronics module 100 is positioned in the pocket 201 and the garment 200 is worn by a wearer. The mobile device 300 may be brought into proximity with the pocket 201 to obtain the electronics module identifier. A camera of the mobile device 300 may then capture image data including the machine-readable code 203. This is then used by the mobile device 300 to form an association between the electronics module 100 and the garment 200. For example, the mobile device 300 may store the electronics module identifier and the wearable article identifier 203 together in a database 301. In other examples, the mobile device 300 may transmit the electronics module identifier and wearable article identifier 203 to an external apparatus which maintains the database 301.

The wearable article identifier 203 may be, for example, derived from a proprietary garment manufacturer identifier. The wearable article identifier 203 may be an identifier for a wearer that wears the garment 200. That is, the wearable article identifier 203 may be a unique identifier for a particular wearer. The wearable article identifier 203 may comprise a combination of a garment manufacturer identifier and a wearer identifier. The wearable article identifier 203 may comprise a username or number such as a jersey number used in athletics.

The present disclosure means that limited manual input is required to form an association between an electronics module identifier and a wearable article identifier 203. A wearer is not required to manually input or select electronics module identifiers and wearable article identifiers 203 via an interface of the mobile device 300 and is not required to form the association manually. Instead, the wearer may simply tap the mobile device 300 against the wearable assembly 10 to read the electronics module identifier and the use the mobile device 300 to read the machine-readable code 203. The wearer may be prompted to perform these steps by an application running on the mobile device 300. Once the electronics module identifier and wearable article identifier 203 are obtained, the mobile device 300 may automatically form the association between the electronics module identifier and the wearable article identifier 203 without further wearer input.

The present disclosure is not limited to electronics modules 100 that communicate with mobile devices 300 and instead may communicate with any electronic device capable of communicating directly with the electronics module 100 or indirectly via an external apparatus over a wired or wireless communication network. The electronic device may be a wireless device or a wired device. The wireless/wired device may be a mobile phone, tablet computer, gaming system, MP3 player, point-of-sale device, or wearable device such as a smart watch. A wireless device is intended to encompass any compatible mobile technology computing device that connects to a wireless communication network, such as mobile phones, mobile equipment, mobile stations, user equipment, cellular phones, smartphones, handsets or the like, wireless dongles or other mobile computing devices. The wireless communication network is intended to encompass any type of wireless such as mobile/cellular networks used to provide mobile phone services.

Figure 2:
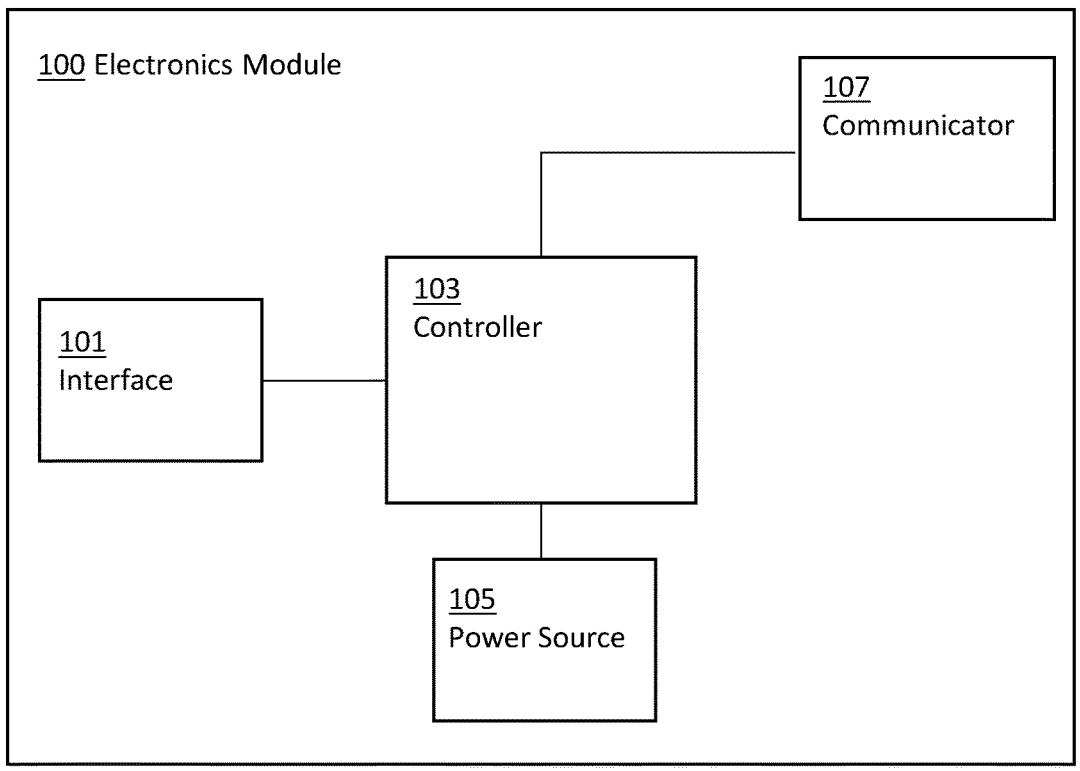
FIG. 2 shows a schematic diagram of an example electronics module according to aspects of the present disclosure.

Referring to FIG. 2, there is shown a schematic diagram for the electronics module 100 of FIG. 1.

The electronics module 100 comprises an interface 101, a controller 103, a power source 105, and a communicator 107.

The interface 101 is arranged to communicatively couple with sensing components of the garment 200 (FIG. 1) to receive signals from the sensing components. The controller 103 is communicatively coupled to the interface 101 and is arranged to receive the signals from the interface 101. The interface 101 may form a conductive coupling or a wireless (e.g. inductive) communication coupling with the electronics components of the wearable article The power source 105 is coupled to the controller 103 and is arranged to supply power to the controller 103. The power source 105 may comprise a plurality of power sources. The power source 105 may be a battery. The battery may be a rechargeable battery. The battery may be a rechargeable battery adapted to be charged wirelessly such as by inductive charging. The power source 105 may comprise an energy harvesting device. The energy harvesting device may be configured to generate electric power signals in response to kinetic events such as kinetic events performed by a wearer of the garment. The kinetic event could include walking, running, exercising or respiration of the wearer. The energy harvesting material may comprise a piezoelectric material which generates electricity in response to mechanical deformation of the converter. The energy harvesting device may harvest energy from body heat of a wearer of the garment. The energy harvesting device may be a thermoelectric energy harvesting device. The power source may be a super capacitor, or an energy cell.

The communicator 107 is arranged to communicatively couple with the mobile device 300 over a wireless communication protocol. The wireless communication protocol may be a near field communication (NFC) protocol but is not limited to any particular communication protocol. The communicator 107 may transmit activity data obtained from the sensing component to the mobile device 300. The activity data may be a processed version of the signals obtained from the sensing component/In an example operation, the mobile device 300 is brought into proximity with the electronics module 100. In response to this, the electronics module 100 is configured to energize the communicator 107 to transmit the electronics module identifier to the mobile device 300 over a wireless communication protocol. Beneficially, this means that the act of the mobile device 300 approaching the electronics module 100 triggers the communicator 107 to transmit the electronics module identifier to the mobile device 300. This provides a simple and intuitive mechanism for transmitting the electronics module identifier to the mobile device 300 which does not require the wearer to manually input the identifier via a user interface of the mobile device 300 for example. The electronics module 100 may listen out for a break in the near field of the communicator 107 antenna caused by the mobile device 300 approaching the communicator 107. This detection of a disruption in the near field will be used to trigger the communicator 107 to transmit the electronics module identifier to the mobile device 300.

The electronics module identifier is a unique identifier for the electronics module 100 that enables the mobile device 300 to uniquely identify the electronics module 100. The electronics module identifier may be an address for the electronics module 100 such as a MAC address or Bluetooth® address or may be a component of an address for the electronics module identifier.

In some examples, the communicator 107 is a component of a passive tag such as a passive Radio Frequency Identification (RFID) tag or Near Field Communication (NFC) tag. These tags comprise an antenna as well as a memory which stores the information, and a radio chip. The mobile device 300 is powered to induce a magnetic field in an antenna of the mobile device 300. When the mobile device 300 is placed in the magnetic field of the antenna of the communicator 107, the mobile device 300 induces current in the antenna of the communicator 107. This induced current is used to retrieve the electronics module identifier from the memory of the tag and transmit the same back to the mobile device 300.

In other examples, the communicator 107 is not a component of a tag. In these examples, the electronics module 100 may detect a mobile device 300 being brought into proximity with electronics module 100 based on factors such as through a sensor of the electronics module 100 or a current being induced in an antenna of the communicator 107. Once the electronics module 100 determines that the mobile device 300 is in proximity with the electronics module 100, the controller 103 reads the electronics module identifier from the memory of the controller 103 or an external memory and energizes the communicator 107 to transmit the electronics module identifier Beneficially, this approach provides greater customisability and allows for different information and dynamically changing information to be transmitted by the communicator 107. That is, the information transmitted by the first antenna 107 can be dynamically changed, e.g. to dynamically change the electronics module identifier. This is because the controller 103 is able to update the content stored in the memory which is not possible in a passive NFC or RFID tag. This is particularly beneficial if it is desirable to update or modify the electronics module identifier that is transmitted to the mobile device 300.

The communicator 107 is not limited to transmitting over the wireless communication protocols described above. The communicator 107 may be a mobile/cellular communicator operable to communicate the data wirelessly via one or more base stations. The communicator 107 may provide wireless communication capabilities for the electronics module 100 and enable the electronics module 100 to communicate via one or more wireless communication protocols such as used for communication over: a wireless wide area network (WWAN), a wireless metroarea network (WMAN), a wireless local area network (WLAN), a wireless personal area network (WPAN), Bluetooth® Low Energy, Bluetooth® Mesh, Bluetooth® 5, Thread, Zigbee, IEEE 802.15.4, ANT, ANT+, a near field communication (NFC), a Global Navigation Satellite System (GNSS), a cellular communication network, or any other electromagnetic RF communication protocol. The cellular communication network may be a fourth generation (4G) LTE, LTE Advanced (LTE-A), LTE Cat-M1, LTE Cat-M2, NB-IoT, fifth generation (5G), sixth generation (6G), and/or any other present or future developed cellular wireless network. A plurality of communicators may be provided for communicating over a combination of different communication protocols.

The electronics module 100 may comprise a Universal Integrated Circuit Card (UICC) that enables the wearable article to access services provided by a mobile network operator (MNO) or virtual mobile network operator (VMNO). The UICC may include at least a read-only memory (ROM) configured to store an MNO/VMNO profile that the electronics module 100 can utilize to register and interact with an MNO/VMNO. The UICC may be in the form of a Subscriber Identity Module (SIM) card. The electronics module 100 may have a receiving section arranged to receive the SIM card. In other examples, the UICC is embedded directly into the controller 103. That is, the UICC may be an electronic/embedded UICC (eUICC). A eUICC is beneficial as it removes the need to store a number of MNO profiles, i.e. electronic Subscriber Identity Modules (eSIMs). Moreover, eSIMs can be remotely provisioned to electronics module 100. The electronics module 100 may comprise a secure element that represents an embedded Universal Integrated Circuit Card (eUICC).

Figure 3:
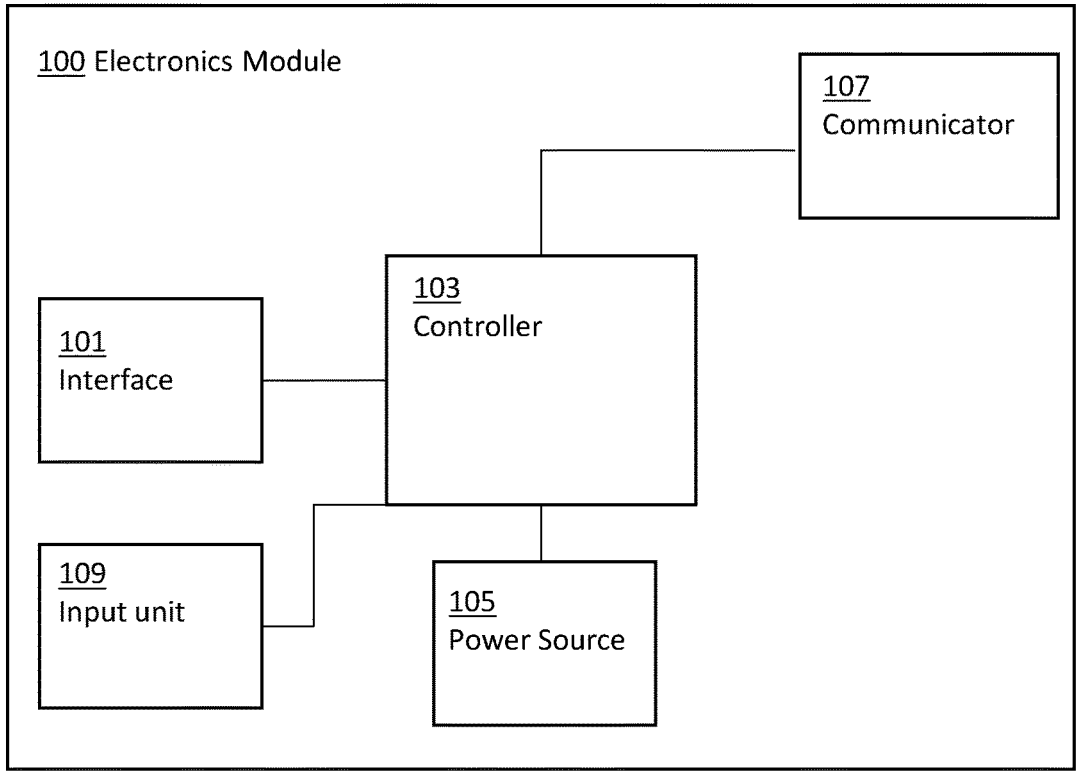
FIG. 3 shows a schematic diagram of another example electronics module according to aspects of the present disclosure.

Referring to FIG. 3, there is shown a schematic diagram of another example electronics module 100 according to aspects of the present disclosure. The electronics module 100 comprises an interface 101, a controller 103, a power source 105, a communicator 107, and an input unit 109. The interface 101, controller 103, power source 105, and communicator 107 are the same as described in reference to FIG. 2.

The input unit 109 is arranged to detect the mobile device 300 being brought into proximity with the electronics module 100. The input unit 109 may comprise a button such as a mechanical push button which is actuated when a mobile device 300 is brought into proximity with the push button. The input unit 109 preferably comprises a sensor 109 such as a proximity sensor or motion sensor.

In the example of FIG. 3, the sensor 109 is a motion sensor that is arranged to detect a displacement of the electronics module 100 caused by the mobile device being brought into proximity with the electronics module 100. These displacements of the electronics module 100 may be caused by the mobile device 300 being tapped against the electronics module 100. Physical contact between the mobile device 300 and the electronics module 100 is not required as the electronics module 100 may be in a holder such as a pocket of a wearable article. This means that there may be a fabric (or other material) barrier between the electronics module 100 and the mobile device 300. In any event, the electronics module 100 being brought into contact with the fabric of the pocket will cause an impulse to be applied to the electronics module 100 which will be sensed by the sensor 109.

The sensor 109 may comprise an inertial measurement unit. The inertial measurement unit may comprise an accelerometer and optionally one or both of a gyroscope and a magnetometer. A gyroscope/magnetometer is not required in all examples, and instead only an accelerometer may be provided, or a gyroscope/magnetometer may be present but put into a low power state. A processor of the sensor 109 may perform processing tasks to classify different types of detected motion. The processor of the sensor 109 may perform machine-learning functions so as to perform this classification. Performing the processing operations on the sensor 109 rather than the controller 103 is beneficial as it reduces power consumption and leaves the controller 103 free to perform other tasks. In addition, it allows for motion events to be detected even when the controller 103 is operating in a low power mode. The sensor 109 communicates with the controller 103 over a serial protocol such as the Serial Peripheral Interface (SPI), Inter-Integrated Circuit (I2C), Controller Area Network (CAN), and Recommended Standard 232 (RS-232). Other serial protocols are within the scope of the present disclosure. The sensor 109 is also able to send interrupt signals to the controller 103 when required so as to transition the controller 103 from a low power mode to a normal power mode when a motion event is detected. The interrupt signals may be transmitted via one or more dedicated interrupt pins. Activity data recorded by the inertial measurement unit may be transmitted to the mobile device 300.

In an example operation, the electronics module 100 is operating in a low power mode. In this low power mode, the majority of the components of the electronics module 100 are not operating so as to save power. For example, the communicator 107 is not energized to transmit data and the controller 103 is not activated to process signal data received via the interface 101. The sensor 109 is supplied with power during the low power mode and is arranged to sense motion data. The sensor 109 may not have full functionality in the low power mode and may only have the necessary processing power to classify motion events into simple categories such as whether a tap has occurred. More computationally expensive processing operations may be disabled during the low power mode. In response to the sensor 109 detecting a tap event, the sensor 109 sends an interrupt to the controller 103. As a result, the controller 103 wakes up from the low power mode and polls the sensor 109 to determine the reason for the interrupt being sent. The sensor 109 responds with a signal indicating that a tap has been detected. The controller 103 then begins the process for controlling the communicator 107 to transmit the electronics module identifier. In particular, the controller 103 reads the electronics module identifier from a memory of the electronics module 100 and energizes the communicator 107 to transmit the information such as the unique identifier.

Figure 4:
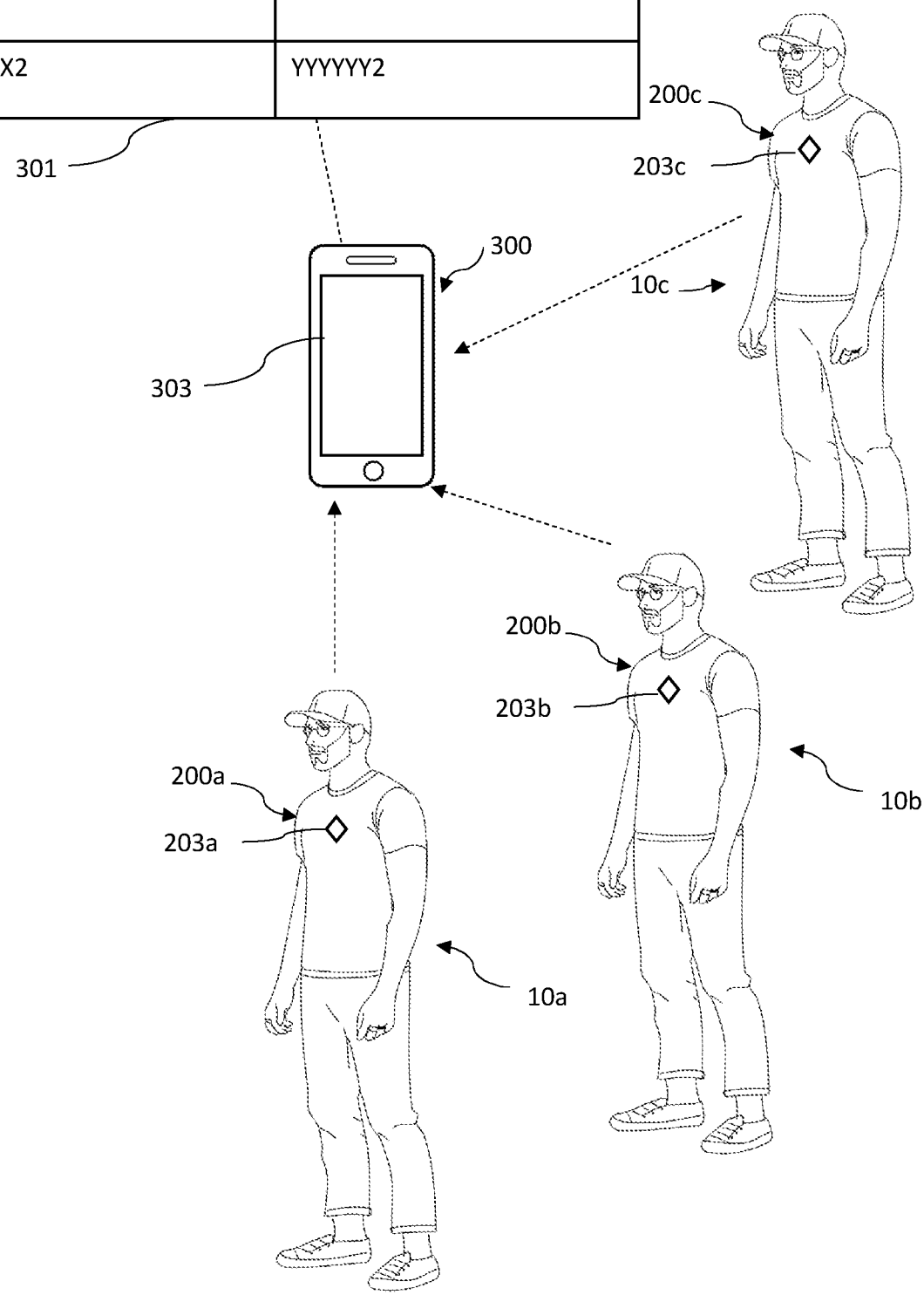
FIG. 4 shows a schematic diagram of another example system according to aspects of the present disclosure.

Referring to FIG. 4, there is shown another example system 1 according to aspects of the present disclosure.

The system 1 comprises a plurality (three in this example) of wearable assemblies 10a, 10b, 10c each worn by a different wearer and a base station 300 which in this example is a mobile device 300. The wearable assemblies 10a, 10b, 10c include electronics modules provided in an inner garment layer which is not visible in FIG. 4. The wearable assemblies 10a, 10b, 10c further comprise an outer garment 200a, 200b, 200c which each comprise a (potentially unique) wearable article identifier in the form of a machine-readable code 203a, 203b, 203c. These outer garments 200a, 200b, 200c may not comprise any sensing components. The sensing functionality may be provided by the electronics modules alone or by the electronics modules interfacing with sensing components such as electrodes provided in the inner garment layer.

During an initial registration stage, for each wearer, the mobile device 300 associates the outer garment 200a, 200b, 200c worn by the wearer with the electronics module provided in the inner garment layer worn by the same wearer. To do this, the mobile device 300 is brought into proximity with the electronics module of the wearable assembly 10a, 10b, 10c to obtain the electronics module identifier. This may be performed by tapping the mobile device 300 against the outer garment 200a, 200b, 200c in the vicinity of the electronics module. The mobile device 300 then reads the machine-readable code of the outer garment 200a, 200b, 200c to obtain the wearable article identifier. In particular, the camera of the mobile device 300 captures an image of the outer garment 200a, 200b, 200c and reads the machine-readable code from the captured image. The first mobile device 300 then forms the association between the electronics module identifier and the wearable article identifier 203a, 203b, 203c for the wearable assembly 10a, 10b, 10c and stores this association in database 301. The present disclosure thus provides a convenient and user-friendly method by which associations are formed between individuals wearing the wearable assemblies 10a, 10b, 10c and the electronics modules of the wearable assemblies 10a, 10b, 10c.

Subsequently, the first mobile device 300 is in communication with each of the electronics modules and is able to receive activity data therefrom. Because the association between electronics module identifier and the wearable article identifier has been formed, the mobile device 300 is able to determine which garment, and thus which wearer, the received activity data relates to. In particular, the mobile device 300 can obtain the electronics module identifier from incoming activity data and compare this electronics module identifier to the database 301 to determine the wearable article identifier that the electronics module identifier is associated with.

In some situations, it is desirable for an operator of the mobile device 300 to quickly view activity data for a particular wearer 10a, 10b, 10c. For example, the operator of the mobile device 300 may be a coach of a sports team who desires to view activity data for a particular athlete. This may help the coach make an assessment of whether the athlete is fatigued and/or at risk of injury. The display of the mobile device 300 may display activity data for a number of wearers at the same time, but this may limit the amount and type of data that is displayed and it may be difficult for the operator to quickly determine a status of the athlete. The operator could manually enter athlete identification information such as a name or player number into an application running on the mobile device 300 to obtain the activity data, but this is user intensive and prone to error.

Beneficially, aspects of the present disclosure provide an improved and more user intuitive mechanism for obtaining activity data associated with a specific garment 200a, 200b, 200c and thus a specific wearer 10a, 10b, 10c. In particular, the operator of the mobile device 300 is able to use a reader of the mobile device 300 to read the machine-readable code of the garment 200a, 200b, 200c worn by the wearer that the operator desires to view data for. The mobile device 300 obtains the wearable article identifier from the machine-readable code 203a, 203b, 203c and then inspects the database 301 to identify the electronics module identifier associated with the wearable article identifier. The mobile device 300 can then fetch activity data for the identified electronics module and display the activity data, such as by displaying a representation thereof, on the display 303 of the mobile device 300.

Figure 5:
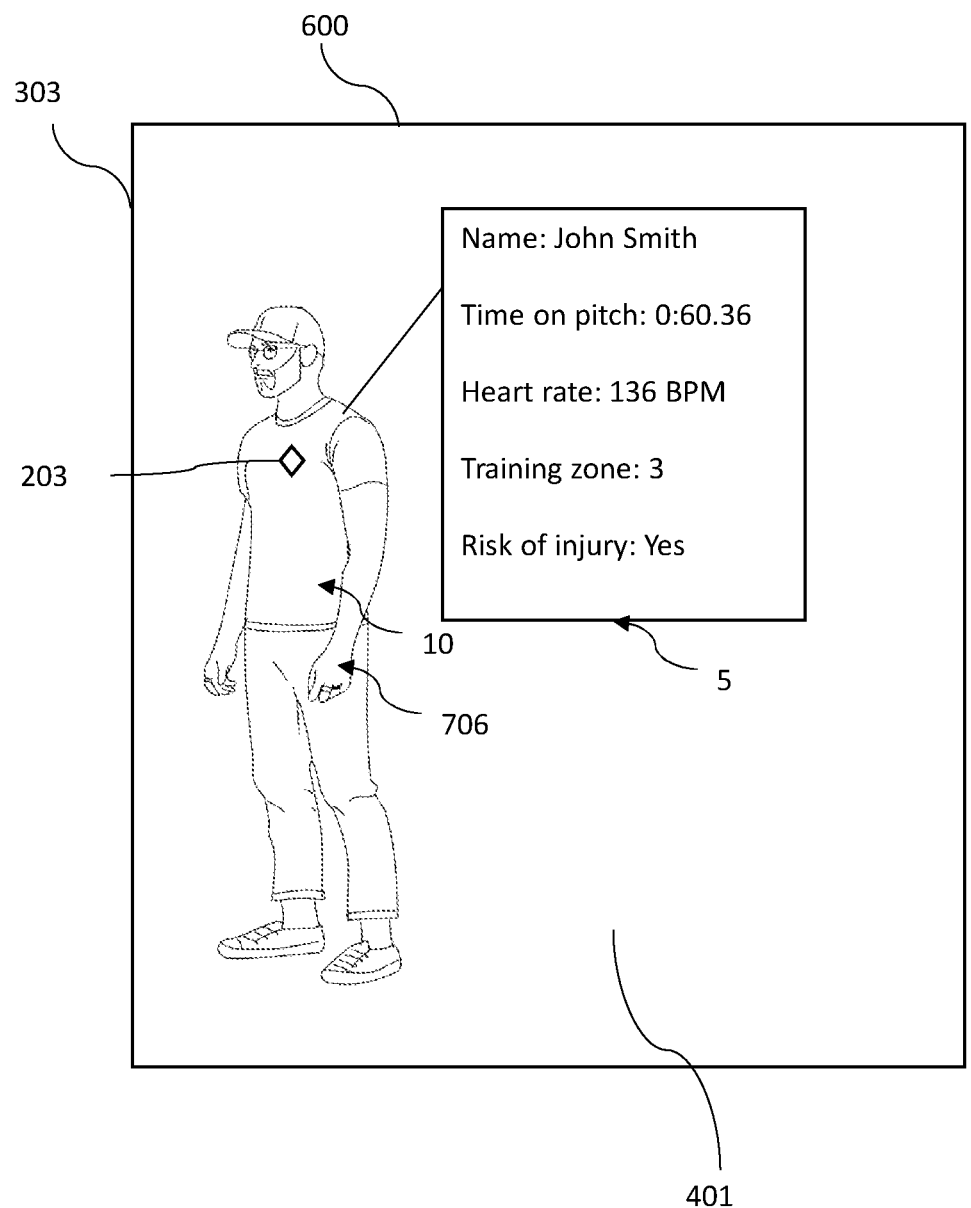
FIG. 5 shows an example interface according to aspects of the present disclosure.

Referring to FIG. 5, there is shown an example interface 600 displayed on the display 303 of the mobile device 300. The interface 600 includes a live view image 401 that is captured by a camera of the mobile device 300. The live view image 401 includes wearer 706 wearing the wearable assembly 10. The wearer 706 is the wearer that the user of the mobile device 300 desires to view activity data for, and the operator has positioned the reader of the mobile device 300 such that the reader captures an image of the wearable assembly 10. This enables the mobile device 300 to obtain the machine-readable code 203 from the image and use this to obtain the wearable article identifier.

The interface 600 further includes a text box 5 that overlays the live view image and includes information for the wearer 706. The information includes activity data obtained from an electronics module worn by the wearer 706. In this example, the activity data comprises cardiac activity data and the text box display information related to the cardiac performance of the wearer 706 including their heart rate, the training zone they are operating in, and whether they are at risk of injury. This information enables the operator to make a rapid assessment of the performance of the wearer 706.

Figure 6:
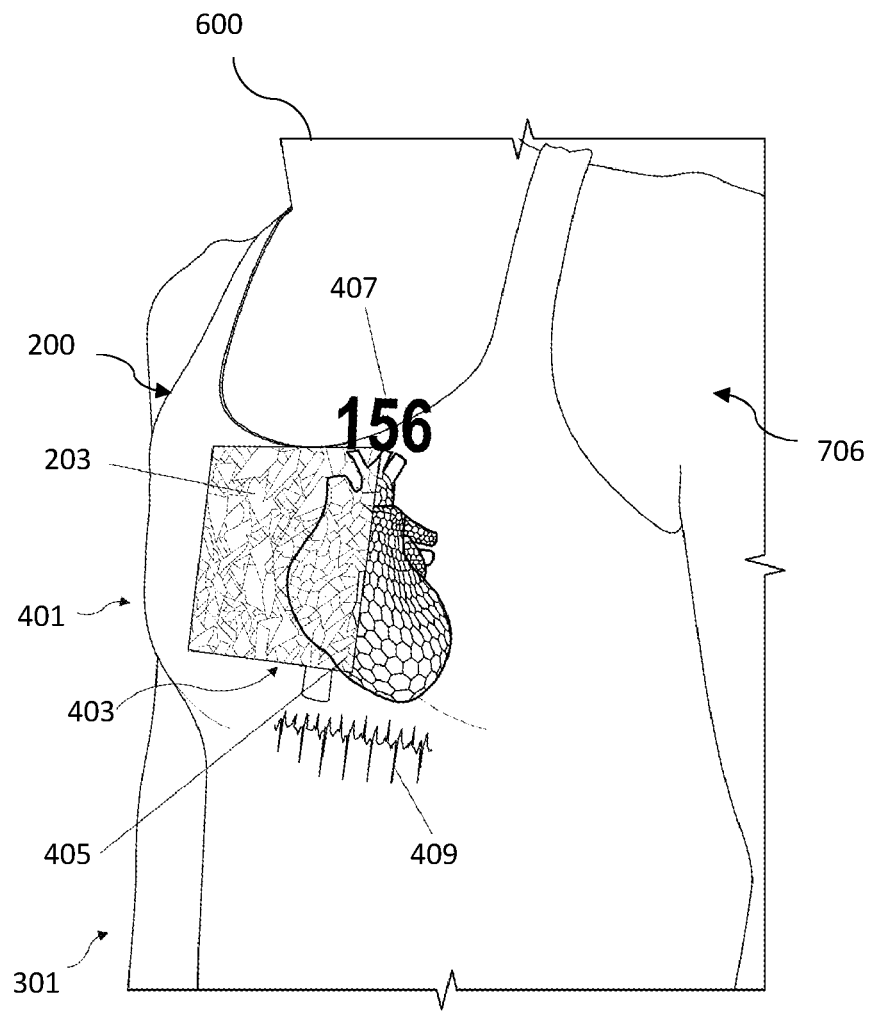
FIG. 6 shows another example interface according to aspects of the present disclosure.

Referring to FIG. 6, there is shown another example interface 600 displayed on the display 301 of the mobile device 300. The interface 600 displays a live view image 401 that is captured by the camera of the mobile device 300. The live view image 401 is a live video feed that currently contains the wearer 706 that the user of the mobile device 300 desires to view activity data for.

The garment 200 has a machine-readable code 203 that comprises the wearable article identifier. The machine-readable code 203 in this example is in the form of a fiducial marker 203 located on an outside surface of the garment 200. Beneficially, the fiducial marker 203 not only includes the wearable article identifier but also enables motion tracking to be performed.

In this example, the mobile device 300 uses the received activity data to augment the live view image 401 displayed on the interface 600. In this example, the received activity data comprises ECG data for the wearer 706. The application running on the mobile device 300 uses the ECG data to generate an augmented reality object 403. The augmented reality object 403 is displayed at a position determined based on the location of the fiducial marker 203. The effect of this is that the augmented reality object 403 appears on the display to overlay the cardiac region of the wearer of the garment 200. The augmented reality object 403 provides a representation of the ECG data.

The augmented reality object 403 comprises a 3D model of the heart 405 that is animated to beat at a rate corresponding to the heart rate of the wearer 706. The 3D model of the heart 405 changes colour based on the heart rate of the wearer 706. The 3D model of the heart 405 is green when the heart rate is at a low value (e.g. less than 100 beats per minute), yellow when the heart rate is at a medium value (e.g. between 100 and 145 beats per minute) and red when the heart rate is at a high value (e.g. greater than 145 beats per minute). Of course, other colours may be used. The 3D model of the heart may additionally or separately change size, shape or texture depending on the heart rate.

The augmented reality object 403 comprises a numerical display of the heart rate 407. The augmented reality object 403 comprises a display of ECG data 409. The display of the heart rate 407 and the ECG data 409 may also change colour, size, shape or texture depending on the heart rate. Conveniently, the present invention conveys cardiac information to the observer in a way that is easy and intuitive to understand as the augmented reality object 403 is positioned to overlay the cardiac region of the user.

Figure 7:
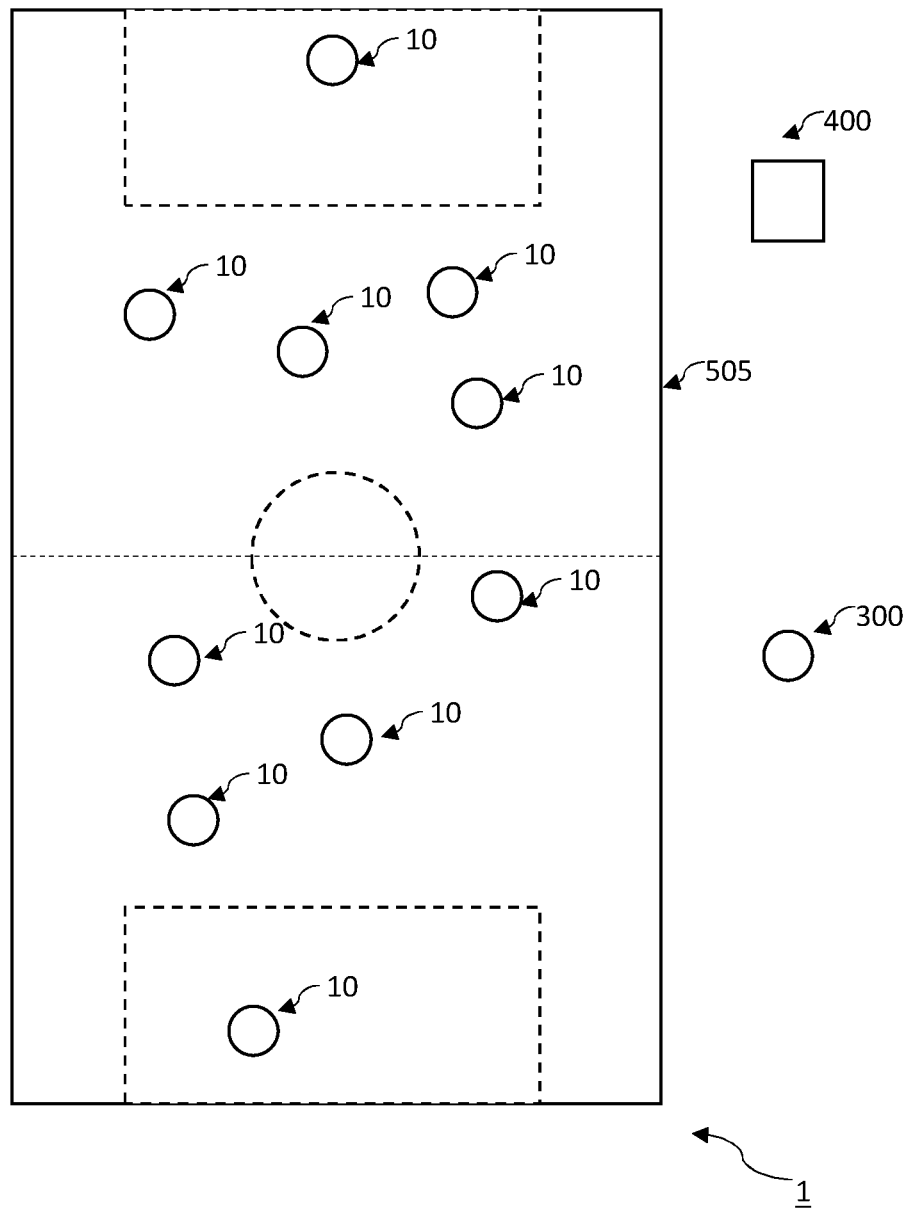
FIG. 7 shows a schematic diagram of yet another system according to aspects of the present disclosure.

Referring to FIG. 7, there is shown an example use case of the system 1 in accordance with the present disclosure. The system 1 comprises a number of wearable assemblies 10 worn by athletes participating in a sports event on a pitch 505. This particular example shows a five-a-side football tournament.

The system 1 further comprises an apparatus 300 such as a mobile device 300 and a base station 400. The base station 400 is in wireless communication with the wearable assemblies 10 and is able to receive activity data from the wearable assemblies 10. The mobile device 300 is operated by a coach or medic on the sidelines of the pitch 505.

Each of the wearable assemblies 10 comprises a garment with a machine-readable code comprising a wearable article identifier and an electronics module that transmits activity data to the apparatus 300. During an initial registration process, for each of the wearable assemblies 10, the electronics module identifier is associated with the wearable article identifier. To do this, the apparatus 300 reads the electronics module identifier and the wearable article identifier for a particular user and associates the electronics module identifier to the wearable article identifier.

In some examples, the base station 400 receives the activity data from the plurality of electronics modules and, for one or a plurality of the electronics modules, transmits the activity data (which may be a processed version of the originally received activity data) and the electronics module identifier to the apparatus 300.

The apparatus 300 uses the received electronics module identifier to identify the wearable article identifier associated with the electronics module identifier. In this way, the apparatus 300 identifies the user wearing the electronics module. The apparatus 300 may then display the activity data along with identifying information for the user. The identifying information may include a username, picture or other identifying information. This approach enables the apparatus 300 to determine which garment and thus which athlete incoming activity data relates to.

In some examples, the base station 400 receives the activity data from the plurality of electronics modules. The operator of the apparatus 300 may desire to view activity data for one or more of the players on the pitch 500. To do this, the operator uses the apparatus 300 to read wearable article identifier for the player or players. The apparatus 300 uses the wearable article identifier to identify the electronics module identifier associated with the wearable article identifier. The apparatus 300 transmits the electronics module identifier to the base station 400 as part of a request for activity data. The base station 400 transmits the activity data (which may be a processed version of the originally received activity data) for the electronics module identified by the electronics module identifier to the apparatus 300. The apparatus 300 may then display the activity data along with identifying information for the user. The identifying information may include a username, picture or other identifying information. This approach enables the apparatus 300 to determine which garment and thus which athlete incoming activity data relates to.

Figure 8:
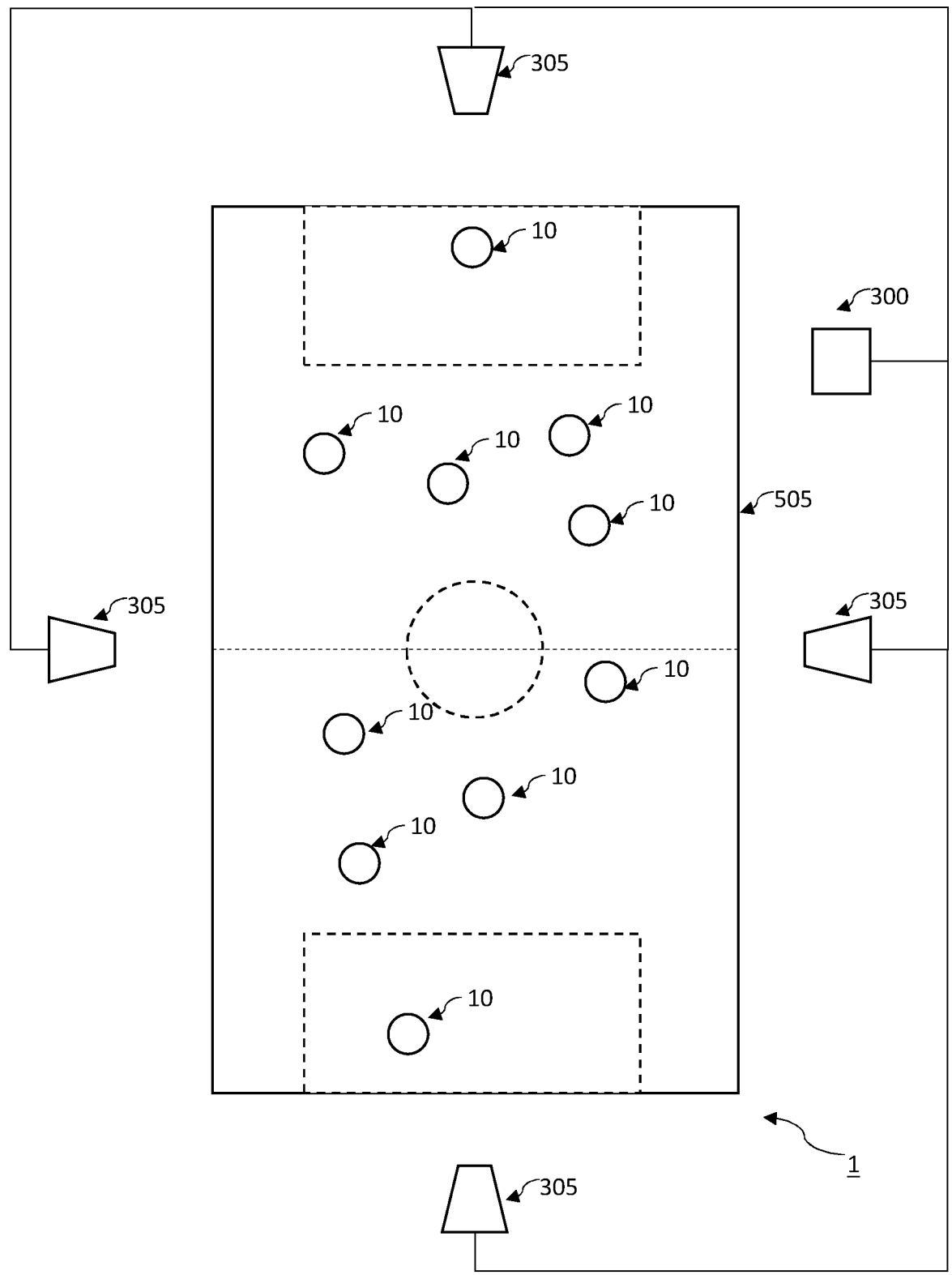
FIG. 8 shows a schematic diagram of yet another system according to aspects of the present disclosure.

Referring to FIG. 8, there is shown an example use case of the system 1 in accordance with the present disclosure. The system 1 comprises a number of wearable assemblies 10 worn by athletes participating in a sports event on a pitch 505. This particular example shows a five-a-side football tournament.

The system 1 further comprises an apparatus 300 which is in wireless communication with the wearable assemblies 10 and is able to receive activity data from the wearable assemblies 10. The data processing apparatus further comprises a plurality of cameras 305 distributed around the pitch 505 which capture live view image data and provide the same to the apparatus 300.

Each of the wearable assemblies 10 comprises a garment with a machine-readable code comprising a wearable article identifier and an electronics module that transmits activity data to the apparatus 300. During an initial registration process, for each of the wearable assemblies 10, the electronics module identifier is associated with the wearable article identifier. In this way, the apparatus 300 is able to determine which garment and thus which athlete incoming activity data relates to. This association may be performed by an external apparatus such as a mobile device.

The apparatus 300 uses the live view image data received from the cameras 305 to generate a video feed for broadcast or distribution using other means. It would be desirable to supplement the generated video feed with the received activity data such as by overlaying representations of the activity data onto the video feed in a manner similar to the examples shown in FIGS. 5 and 6.

To achieve this effect, a human producer could inspect the incoming video feed to determine the athletes contained within the live view image and then fetch activity data for these athletes. However, this approach is labour intensive and prone to error.

Beneficially, in accordance with the present disclosure, the apparatus 300 can identify machine readable code(s) for garment(s) present in the live view image and use this machine-readable code to obtain activity data for the athletes wearing the identified garment(s). In this way, an automatic approach for supplementing image data with activity data is provided which does not require human input.

Figure 9:
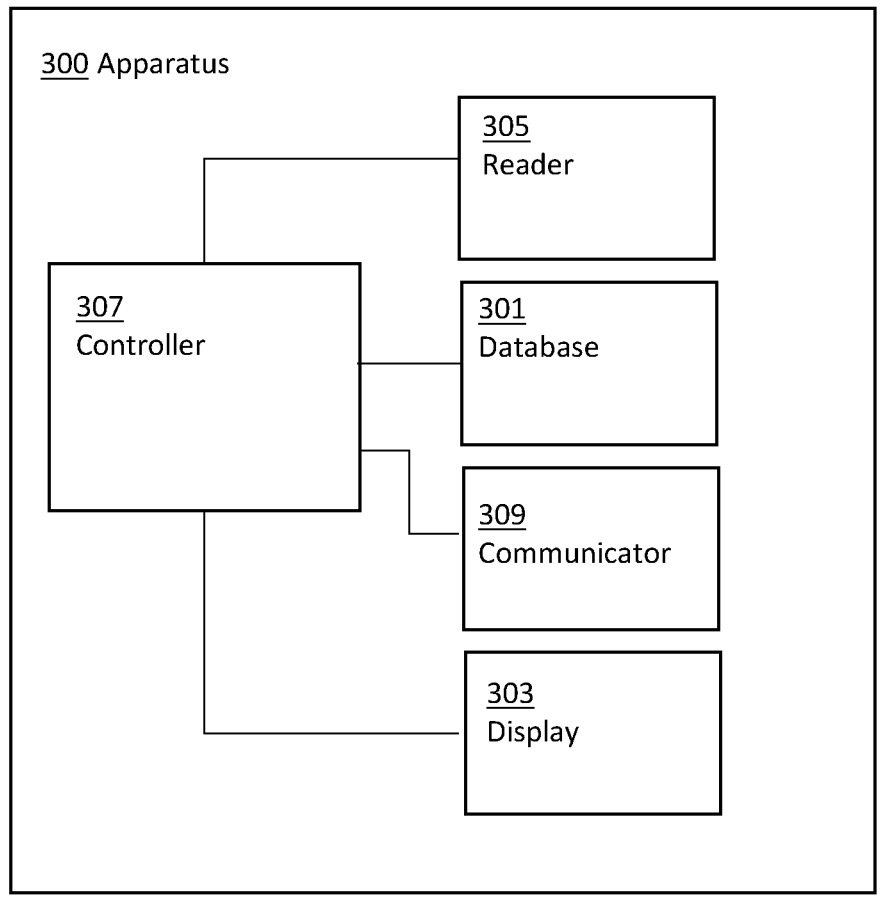
FIG. 9 shows a schematic diagram of an example apparatus according to aspects of the present disclosure.

Referring to FIG. 9, there is shown another example apparatus 300 according to aspects of the present disclosure. The apparatus 300 in the example of FIG. 9 comprises a database 301, display 303, reader 305, controller 307 and communicator 309. It will be appreciated that the apparatus 300 is not required to include all of these components and may comprise additional or separate components.

In some example implementations, the apparatus 300 performs operations to associate an electronics module identifier with a wearable article identifier for a wearable assembly according to aspects of the present disclosure.

In these examples, the communicator 309 is arranged to communicate with the electronics module over a wireless communication protocol to obtain the electronics module identifier.

Further, the reader 305 arranged to read a machine-readable code comprising a wearable article identifier from an outside surface of the garment.

The controller 307 is arranged to associate the electronics module identifier with the wearable article identifier. This may involve the controller 307 storing the electronics module identifier and wearable article identifier on a local database 301. Additionally, or separately, the controller 307 may control the communicator 309 to transmit the associated electronics module identifier and the wearable article identifier to an external apparatus such as a base station.

In some example implementations, the apparatus 300 performs operations to access activity data from an electronics module of a wearable assembly according to aspects of the present disclosure.

In these examples, the reader 305 is arranged to read a machine-readable code comprising a wearable article identifier from an outside surface of the garment of the wearable assembly.

Further, the controller 307 is operable to use the wearable article identifier to identify an electronics module identifier associated with the wearable article identifier. The controller 307 then uses the electronics module identifier to obtain activity data from the electronics module. The activity data is associated with a user wearing the garment. This may involve the controller 307 accessing the local database 301 to determine the electronics module identifier associated with the wearable article identifier, and then accessing locally stored activity data for the identified electronics module. Alternatively, the apparatus 300 may communicate with a server to obtain the activity data.

Figures 10, 11:
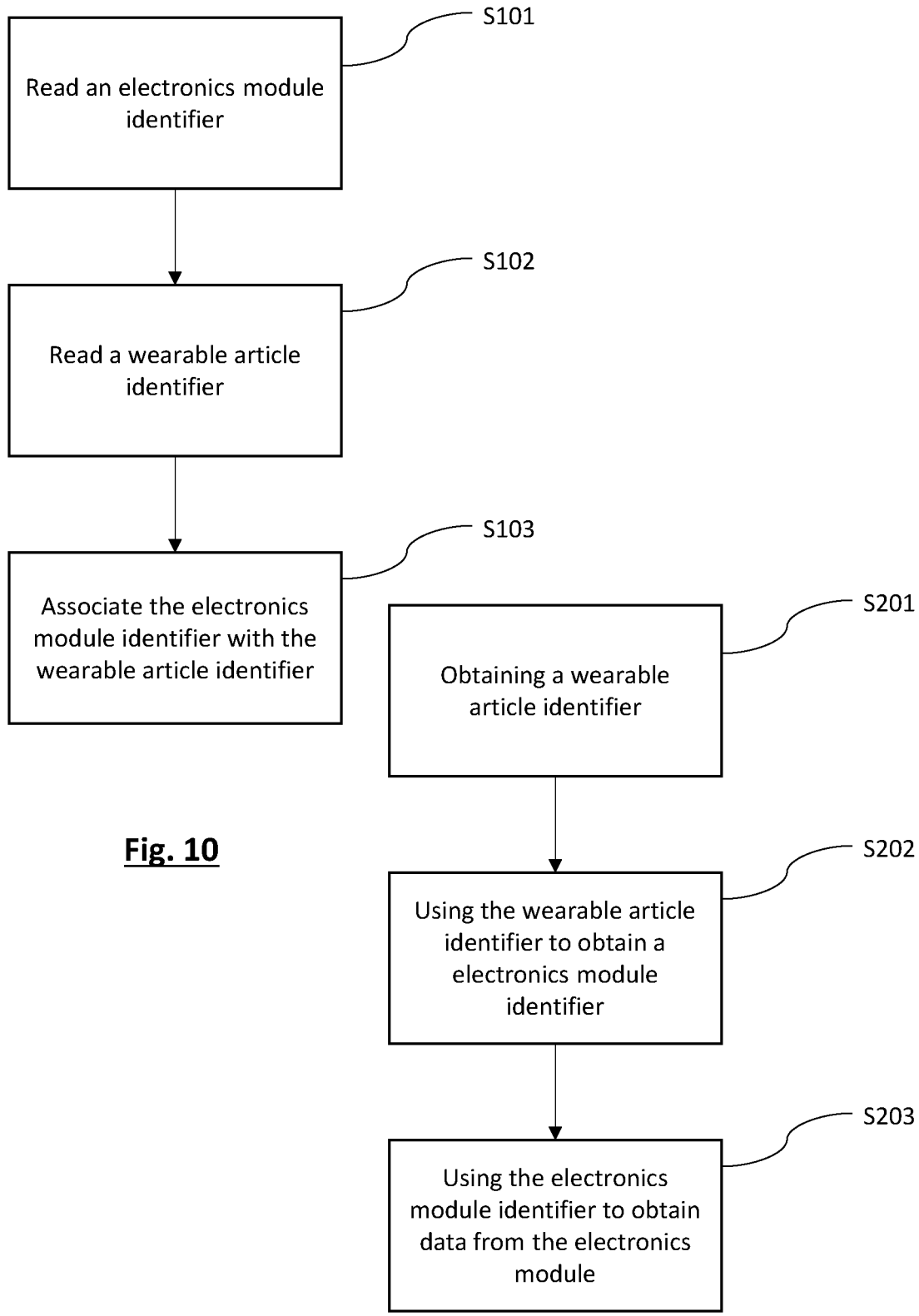
FIG. 10 shows a flow diagram for an example method according to aspects of the present disclosure.
FIG. 11 shows a flow diagram for another example method according to aspects of the present disclosure.

Referring to FIG. 10, there is shown an example method of associating an electronics module with a wearable article for a wearable assembly according to aspects of the present disclosure.

Step S101 of the method comprises reading an electronics module identifier for an electronics module.

Step S102 of the method comprises reading a wearable article identifier for a wearable article associated with the electronics module.

Step S103 of the method comprises associating the electronics module identifier with the wearable article identifier.

Referring to FIG. 11, there is shown an example method of accessing activity data from an electronics module of a wearable assembly according to aspects of the present disclosure.

Step S201 of the method comprises obtaining a wearable article identifier for a wearable article.

Step S202 of the method comprises using the wearable article identifier to identify an electronics module identifier for an electronics module associated with the wearable article identifier.

Step S203 of the method comprises using the electronics module identifier to obtain activity data for the user wearing the wearable article from the electronics module.

Figure 12:
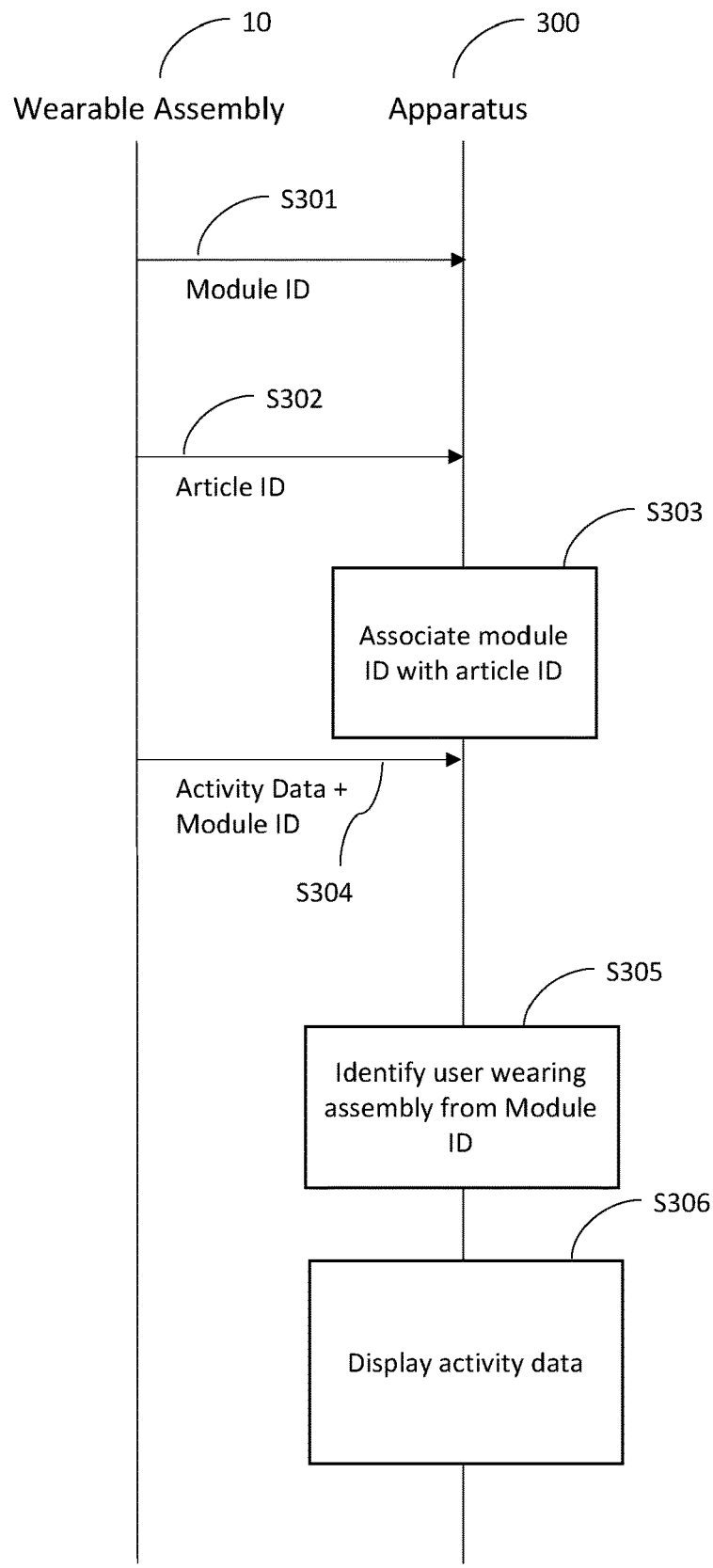
FIG. 12 shows a swim lane diagram for yet another example method according to aspects of the present disclosure.

Referring to FIG. 12, there is shown a swim-lane flow diagram for an example method according to aspects of the present disclosure. The method is performed by a wearable assembly 10 and apparatus 300.

In step S301, the apparatus 300 obtains an electronics module identifier for an electronics module of the wearable assembly 10.

In step S302, the apparatus 300 obtains a wearable article identifier for a wearable article of the wearable assembly 10.

In step S303, the apparatus 300 associates the electronics module identifier with the wearable article identifier.

In step S304, the electronics module of the wearable assembly 10 transmits activity data and the electronics module identifier to the apparatus 300. In some examples, the electronics module identifier is not transmitted as this information may be inferred by the apparatus 300 based on factors such as the properties of the communication and the communication channel used by the electronics module.

In step S305, the apparatus 300 identifies the user wearing the electronics module by identifying the wearable article identifier associated with the electronics module identifier in step S303.

In step S306, the apparatus 300 displays the activity data, optionally along with identifying information for the user.

Figure 13:
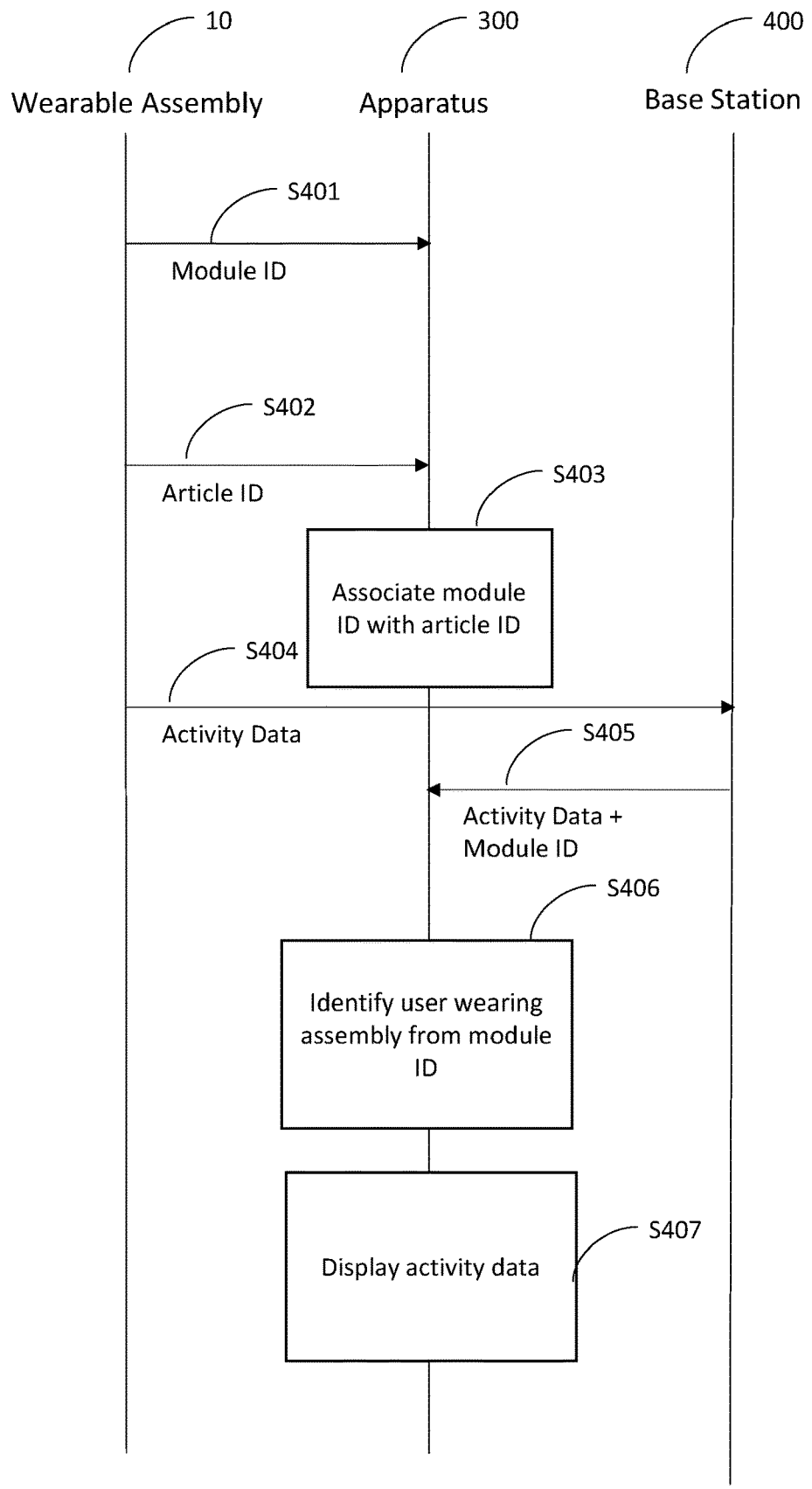
FIG. 13 shows a swim lane diagram for yet another example method according to aspects of the present disclosure.

Referring to FIG. 13, there is shown a swim-lane flow diagram for an example method according to aspects of the present disclosure. The method is performed by a wearable assembly 10, apparatus 300 and base station 400.

In step S401, the apparatus 300 obtains an electronics module identifier for an electronics module of the wearable assembly 10.

In step S402, the apparatus 300 obtains a wearable article identifier for a wearable article of the wearable assembly 10.

In step S403, the apparatus 300 associates the electronics module identifier with the wearable article identifier.

In step S404, the electronics module of the wearable assembly 10 transmits activity data and the electronics module identifier to the base station 400. In some examples, the electronics module identifier is not transmitted as this information may be inferred by the base station 400 based on factors such as the properties of the communication and the communication channel used by the electronics module.

In step S405, the base station 400 transmits the received activity data and the electronics module identifier to the apparatus 300.

In step S406, the apparatus 300 identifies the user wearing the electronics module by identifying the wearable article identifier associated with the electronics module identifier in step S403.

In step S407, the apparatus 300 displays the activity data, optionally along with identifying information for the user.

Figure 14:
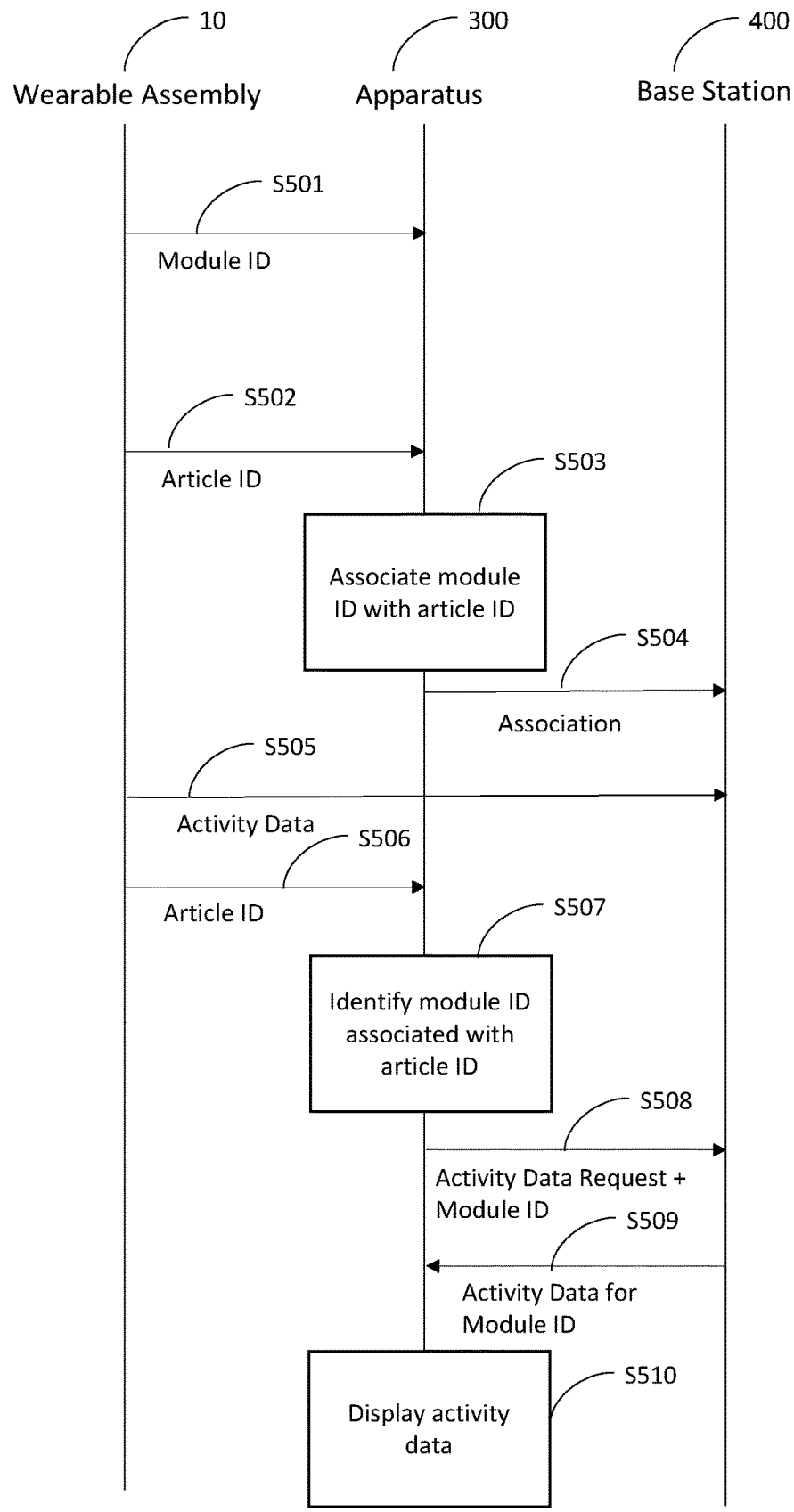
FIG. 14 shows a swim lane diagram for yet another example method according to aspects of the present disclosure.

Referring to FIG. 14, there is shown a swim-lane flow diagram for an example method according to aspects of the present disclosure. The method is performed by a wearable assembly 10, apparatus 300 and base station 400.

In step S501, the apparatus 300 obtains an electronics module identifier for an electronics module of the wearable assembly 10.

In step S502, the apparatus 300 obtains a wearable article identifier for a wearable article of the wearable assembly 10.

In step S503, the apparatus 300 associates the electronics module identifier with the wearable article identifier.

In step S504, the apparatus 300 transmits the association between the electronics module identifier and the wearable article identifier to the base station 400.

In step S505, the electronics module of the wearable assembly 10 transmits activity data to the base station 400 optionally along with the electronics module identifier.

In step S506, the apparatus 300 obtains the wearable article identifier from the wearable assembly 10.

In step S507, the apparatus 300 uses the wearable article identifier to identify an electronics module identifier associated with the wearable article identifier.

In step S508, the apparatus 300 transmits an activity data request comprising the electronics module identifier to the base station 400.

In step S509, the base station 400 transmits the received activity data for the relevant electronics module to the apparatus 300.

In step S510, the apparatus 300 displays the activity data, optionally along with identifying information for the user.

Figure 15:
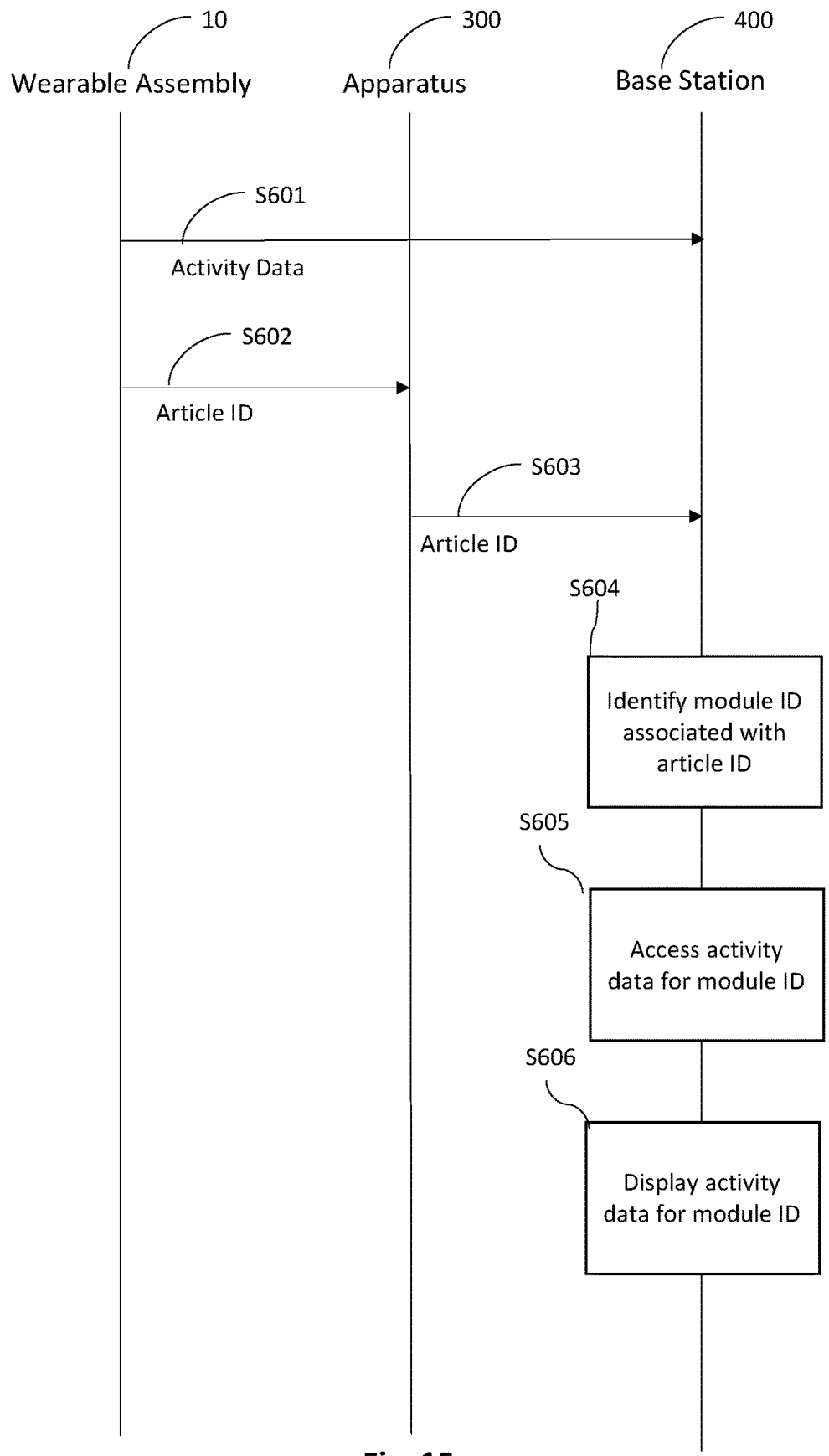
FIG. 15 shows a swim lane diagram for yet another example method according to aspects of the present disclosure.

Referring to FIG. 15, there is shown a swim-lane flow diagram for an example method according to aspects of the present disclosure. The method is performed by a wearable assembly 10, apparatus 300 and base station 400.

In step S601, the electronics module of the wearable assembly 10 transmits activity data to the base station 400 optionally along with the electronics module identifier.

In step S602, the apparatus 300 obtains a wearable article identifier for the wearable article of the wearable assembly 10.

In step S603, the apparatus 300 transmits the wearable article identifier to the base station 400.

In step S604, the base station 400 uses the wearable article identifier to identify an electronics module identifier for an electronics module associated with the wearable article identifier.

In step S605, the base station 400 uses the electronics module identifier to obtain activity data for the user wearing the wearable article from the electronics module.

In step S606, the base station 400 displays the activity data, optionally along with identifying information for the user.

In examples of the present disclosure, the electronics module 100 is removably attached to the wearable article 200 comprising the wearable article identifier 203. In these examples, the wearable article 200 may comprise the sensing components. Alternatively, the sensing components may be provided by the electronics module 100. That is, the electronics module 100 may have integrated sensors such as one or more inertial measurement units, temperature sensors, or Global Navigation Satellite System receiver.

In examples of the present disclosure, the electronics module 100 is separate from the wearable article 200 comprising the wearable article identifier 203. In these examples, the electronics module 100 may be incorporated into a first wearable article worn by the user while a second wearable article 200 worn by the user comprises the wearable article identifier 203. The first wearable article may be an inner garment layer and the second wearable article 200 may be an outer garment layer covering the inner garment layer. The first wearable article may be a wristband and the second wearable article may be a top or an article of headwear such as a hardhat or helmet. Generally, it is preferable for the second wearable article to be visible to others to enable the reading of the machine-readable code.

In the present disclosure, the electronics module may also be referred to as an electronics device or unit. These terms may be used interchangeably. Further, the mobile device may also be referred to as a user electronic device and these terms can also be used interchangeably.

Figure 16:
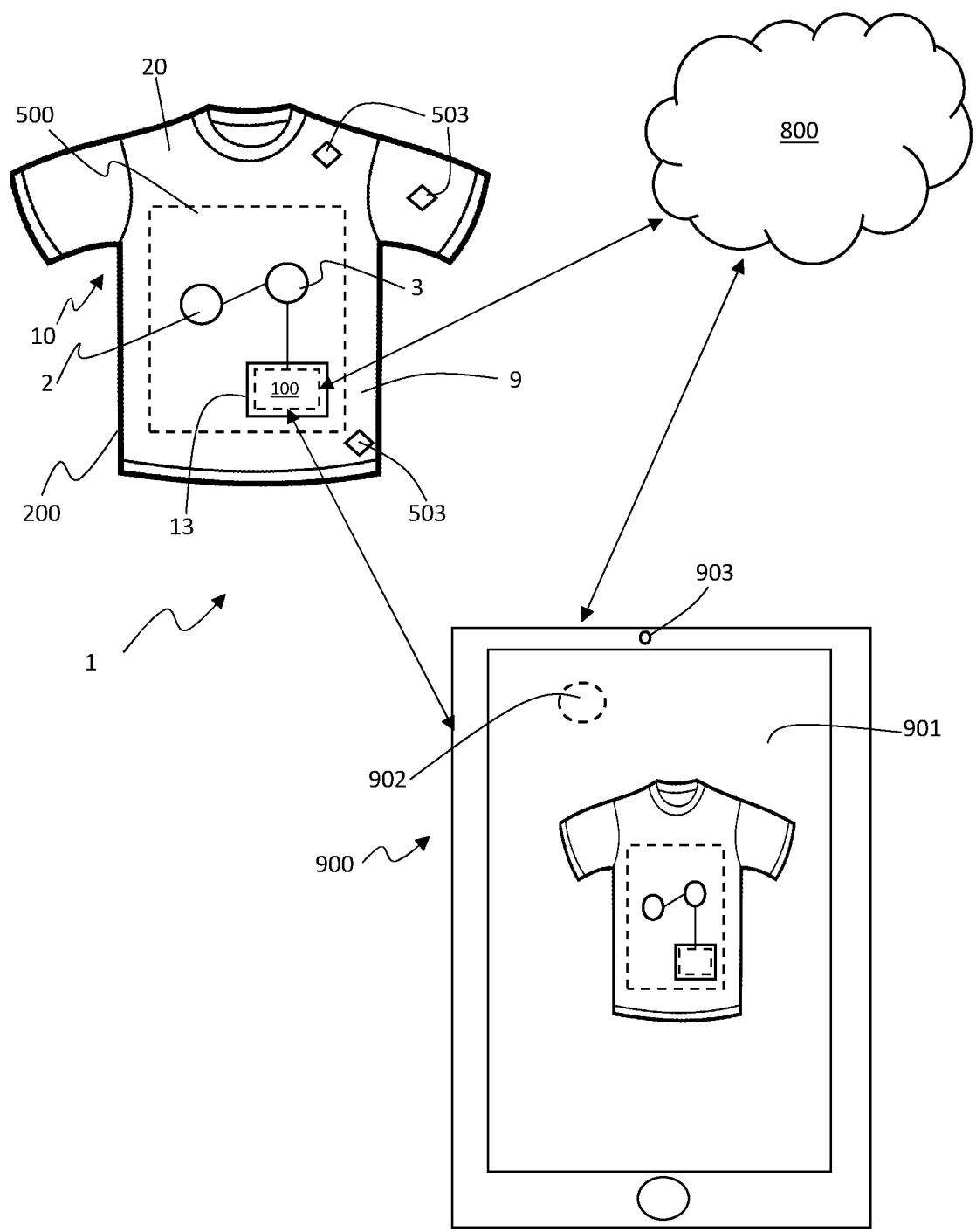
FIG. 16 shows a schematic diagram of an example system according to aspects of the present disclosure.

Referring to FIG. 16, there is shown another example of a garment 200, electronic module 100, a mobile device 900 and server 800 in accordance with aspects of the present invention. The garment 200 in the example of FIG. 16 is in the form of a T-shirt.

The garment 200 comprises first and second layers: an inner garment layer 6 and an outer garment layer 8. In an exemplar embodiment, only the front portion 20 of the main body 9 of the garment 200 comprises a double layer, although in another embodiment, the whole of the garment 200 can be double-layered.

The garment 200 comprises sensing components 2, 3 arranged to monitor the activity of the wearer of the garment 200. The sensing components 2, 3 are communicatively coupled to the electronics module 100 and arranged to communicate activity data to the server 800 or to a user electronic device 900. In the example described herein, two sensing components are described, but it will be evident to a person skilled in the art, that any number of sensing components can be used, depending upon requirements and application.

The sensing components 2, 3 are provided on an outer face 15 off the inner garment layer 6 so that they lie adjacent the skin of the wearer. This enables the sensing components 2, 3 to measure the activity data such as biosignals for the wearer of the garment 200.

The sensing components 2, 3 may be arranged to sense one or more signals external to the user. The sensing components may also comprise any or a combination of a temperature sensor, a camera, a location tracking module such as a GPS module, and a chemical sensor.

As mentioned above, activity data may comprise any or a combination of the different example measurements described above.

The garment 200 and electronics module 100 comprise a wearable assembly 10. The wearable assembly 10, user electronic device 900, and server 800 form an example system 1 in accordance with aspects of the invention.

The electronics module 100 may be located on any suitable portion of the garment 200 as required by the application. In this exemplar embodiment, the electronics module 100 can be held in an electronic module holder in the form of pocket 13 on the outer surface 12 of the outer garment layer 8.

The pocket 13 is sized to receive the electronic module 100. When disposed in the pocket 13, the electronics module 100 is arranged to integrate with the sensing components of garment 200 and receive activity data from the sensing components 2, 3. The electronics module 100 is therefore removable from the garment 200.

As with previous embodiments described herein, the present disclosure is not limited to electronic module holders 13 in the form of a pockets 13. Instead, other mechanism for releasably mechanically coupling the electronics module 100 to the garment 200 may be provided. The mechanical coupling of the electronics module 100 to the garment 200 may be provided by a mechanical interface such as a clip, a plug and socket arrangement, etc. The mechanical coupling or mechanical interface may be configured to maintain the electronics module 100 in a particular orientation with respect to the garment 200 when the electronics module 100 is coupled to the garment 200. This may be beneficial in ensuring that the electronics module 100 is securely held in place with respect to the garment 200 and/or that any electronic coupling of the electronics module 100 and the garment 200 (or a component of the garment 200) can be optimized. The mechanical coupling may be maintained using friction or using a positively engaging mechanism, for example.

Beneficially, the removable electronics module 100 may contain all of the components required for data transmission and processing such that the garment 200 only comprises the sensing components and communication pathways. In this way, manufacture of the garment 200 may be simplified. In addition, it may be easier to clean a garment 200 which has fewer electronic components attached thereto or incorporated therein. Furthermore, the removable electronics module 100 may be easier to maintain and/or troubleshoot than embedded electronics. The electronics module 100 may comprise flexible electronics such as a flexible printed circuit (FPC). The electronics module 100 may be configured to be electrically coupled to the garment 200.

The electronics module 100 transmits the activity data to an external apparatus such as the server 800 and/or the user electronic device 900.

In the exemplar embodiment described herein, the user electronic device 900 is a cellular radio telephone or tablet with wireless communication capabilities as will be described in further detail below.

As described in relation to the first embodiment above, in environments such as team sports or workplace settings, there may be a number of different users wearing different wearable assemblies 10a, 10b, 10c at the same time. Each of the wearable assemblies 10a, 10b, 10c will have a different electronics module 100 transmitting data to the same external apparatus such as user electronic device 900 and/or server 800. The data transmitted by the electronics module 100 will be associated with an electronic module identifier that uniquely identifies the electronics module 100. The electronics module identifier may be, for example, a communication address for the electronics module 100.

As with the first embodiment described above, the garment 200 of the wearable assembly 100 includes a wearable article identifier 500. The wearable article identifier 500 comprises a machine-readable code that is readable remotely. The wearable article identifier 500 identifies the garment 200, and thus the wearer of the garment 200 at a particular time when the wearer is using the electronic module 100. The electronic module identifier is different to the wearable article identifier 500.

The user electronic device 900 communicates with the electronics module 100 to obtain the electronics module identifier for the electronics module 100. The user electronic device 900 also reads the machine-readable code on the garment 200 to obtain the wearable article identifier 500 for the garment 200. The user electronic device 900 then associates the electronics module identifier with the wearable article identifier 500. In this way, when activity data is received from the electronics module 100, the user electronic device 400, having read the wearable article identifier 500 is able to determine that the activity data relates to a particular garment 200 and thus a particular wearer.

In a preferred implementation, the association between the electronics module 100 and the garment 200 is formed once the electronics module 100 is positioned in the pocket 13 and the garment 200 is worn by a wearer. The user electronic device 900 may be brought into proximity with the pocket 13 to obtain the electronics module identifier.

A capturing device, such as a time-of-flight sensor 902, or a camera 903, of the user electronic device 900 may then capture a machine-readable code encoded in the wearable article identifier 500. This is then used by the user electronic device 900 to form an association between the electronics module 100 and the garment 200. For example, the user electronic device 900 may store the electronic module identifier and the wearable article identifier 500 together in a memory 404. In other examples, the user electronic device 900 may transmit the electronic module identifier and wearable article identifier 500 to an external apparatus, such as the server 800 which maintains a database.

As described in relation to the first embodiment, the wearable article identifier 500 may be, for example, derived from a proprietary garment manufacturer identifier. The wearable article identifier 500 may be an identifier for a wearer of the garment. That is, the wearable article identifier 500 may be a unique identifier for a particular wearer. The wearable article identifier 500 may comprise a combination of a garment manufacturer identifier and a wearer identifier. The wearable article identifier 500 may include a username or number such as a jersey number used in athletics.

The user electronic device 900 may be a wireless device or a wired device. The wireless/wired device may be a mobile phone, tablet computer, gaming system, MP3 player, point-of-sale device, or wearable device such as a smart watch. A wireless device is intended to encompass any compatible mobile technology computing device that connects to a wireless communication network, such as mobile phones, mobile equipment, mobile stations, user equipment, cellular phones, smartphones, handsets or the like, wireless dongles or other mobile computing devices. The wireless communication network is intended to encompass any type of wireless such as mobile/cellular networks used to provide mobile phone services.

Figure 17:
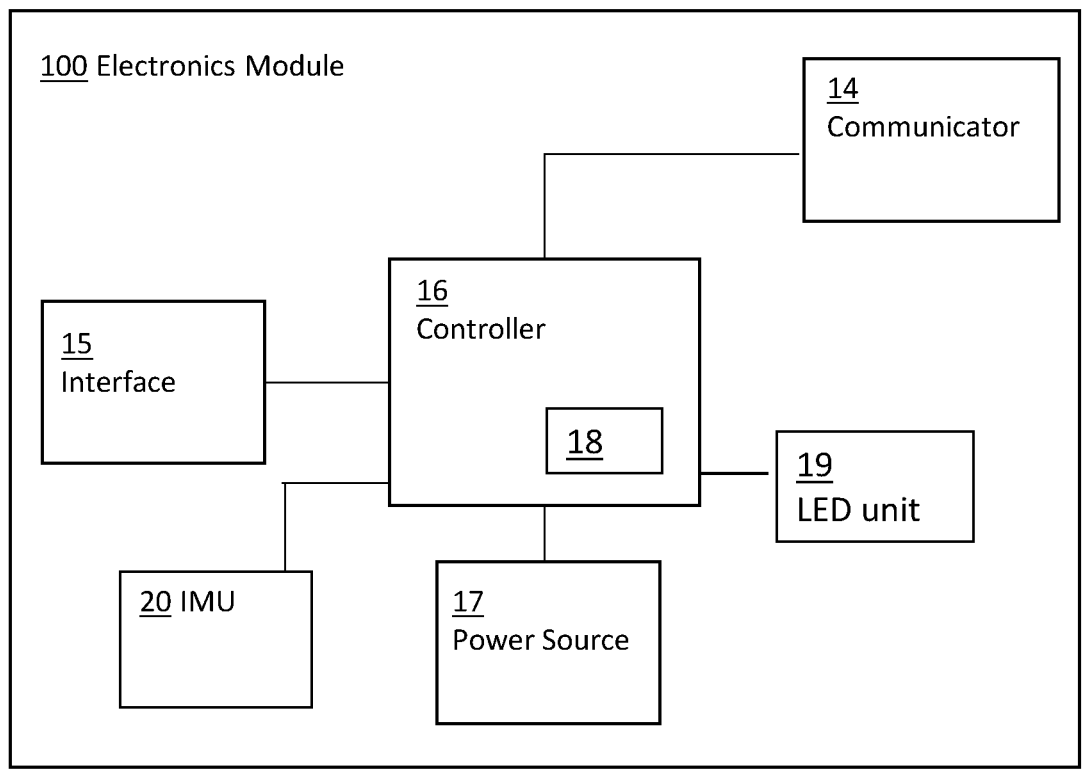
FIG. 17 shows a schematic diagram of an example electronics module according to aspects of the present disclosure.

Referring to FIG. 17, there is shown a schematic diagram for the electronics module 100 of FIG. 16.

As with the electronics module illustrated in FIG. 2, the electronics module 100 comprises an interface 15, a controller 16, a power source 17, and a communicator 14 and operates similarly as described therein.

The interface 15 is arranged to communicatively couple with sensing components 2, 3 of the garment 200 (FIG. 16) so as to receive signals from the sensing components 2, 3. The controller 16 is communicatively coupled to the interface 15 and is arranged to receive the signals from the interface 15. The interface 15 may form a conductive coupling or a wireless (e.g. inductive) communication coupling with the electronics components of the wearable article The power source 17 is coupled to the controller 16 and is arranged to supply power to the controller 16. The power source 17 may comprise a plurality of power sources. The power source 17 may be a battery. The battery may be a rechargeable battery. The battery may be a rechargeable battery adapted to be charged wirelessly such as by inductive charging. The power source 17 may comprise an energy harvesting device. Other power sources as described above in relation to the first embodiment may be used.

The communicator 14 is arranged to communicatively couple with the user electronic device 900 over a wireless communication protocol. The wireless communication protocol may be a near field communication (NFC) protocol but is not limited to any particular communication protocol. Other communication protocols as described above in relation to the first embodiment may be used.

The communicator 14 may transmit activity data obtained from the sensing components 2, 3 to the user electronic device 900 either directly or via, for example, the server 800. The activity data may be a processed version of the signals obtained from the sensing components 2, 3.

In an example operation, the user electronic device 900 is brought into proximity with the electronics module 100. In response to this, the electronics module 100 is configured to energize the communicator 14 to transmit the electronics module identifier to the user electronic device 900 over a wireless communication protocol.

As described above, the electronics module identifier is a unique identifier for the electronics module 100 that enables the user electronic device 900 to uniquely identify the electronics module 100. The electronics module identifier may be an address for the electronics module 100 such as a MAC address or Bluetooth® address or may be a component of an address for the electronics module identifier.

Figure 18:
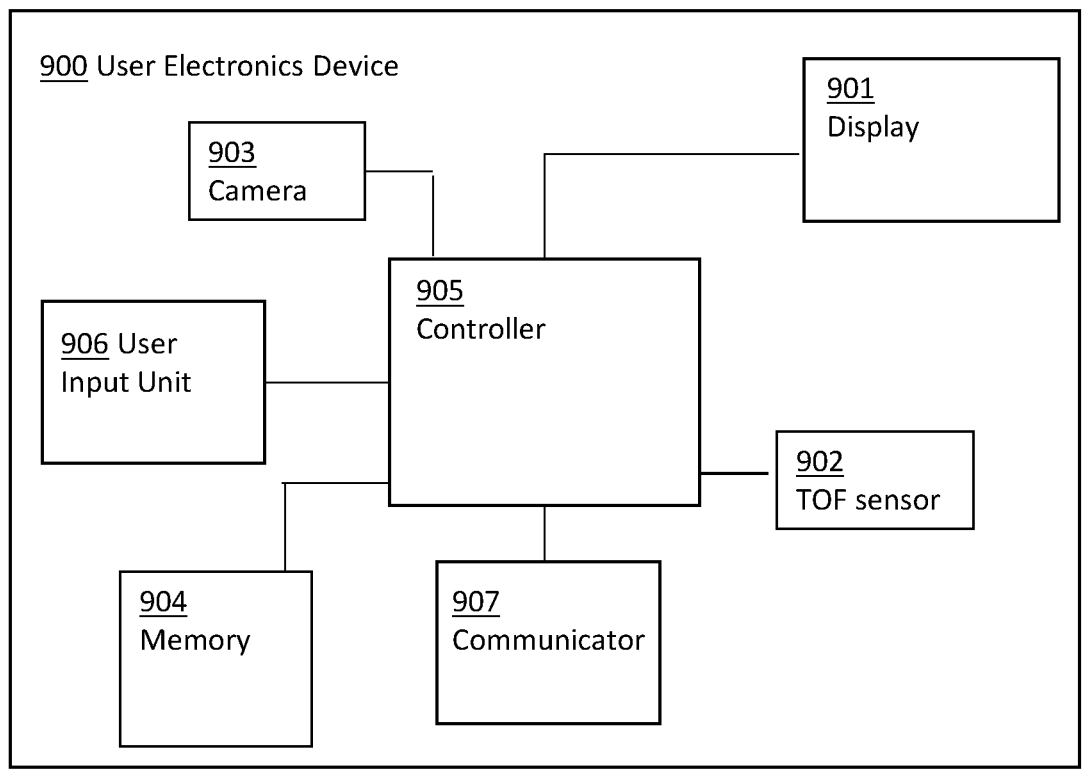
FIG. 18 shows a schematic diagram of an example user electronic device according to aspects of the present disclosure.
Figure 19:
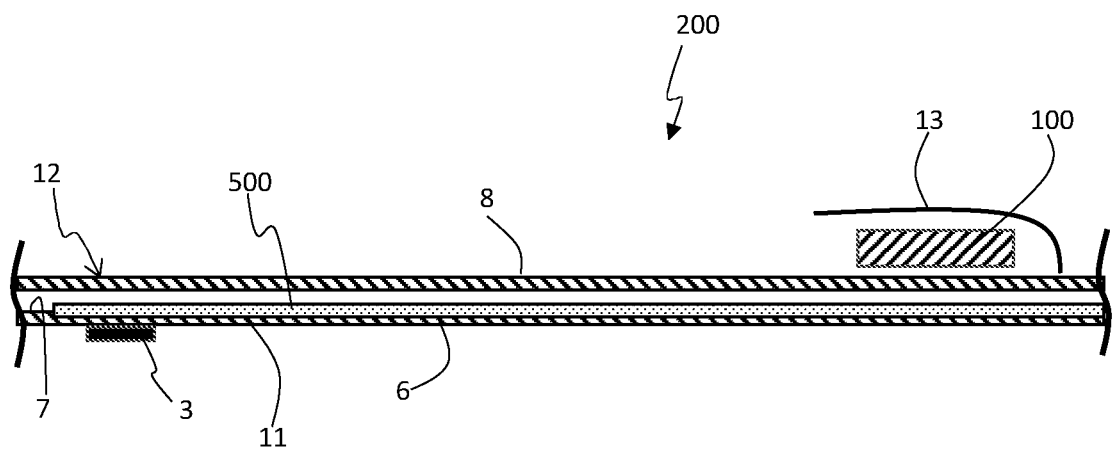
FIG. 19 shows a schematic diagram of a cross section through a portion of a wearable article for a wearable assembly according to aspects of the present disclosure.

The user electronic device 900 in the example of FIG. 18 is in the form of a mobile phone or tablet and comprises a controller 905, a memory 904, a display 901, a user input unit 906, and capturing devices in the form of a time-of-flight (ToF) sensor 902 and a camera 903. The controller 905 provides overall control to the user electronic device 900.

The user input unit 906 receives inputs from the user such as a user credential.

The camera 903 captures the image of the garment 200.

The memory 904 stores information for the user electronic device 900.

The ToF sensor 902 is an infrared sensor. Infrared ToF sensors use a transmitted infrared signal which then senses the infrared signal reflected of distant objects and measures the time it takes for that infrared signal to bounce off of an object and back in order to make measurements of distance between the ToF sensor 902 and the object. These measurements can be used to create three-dimensional representations of objects sensed by the ToF sensor 902. In augmented reality applications ToF sensors are useful in measuring surroundings accurately in three dimensions. It also helps with object detection and recognition.

The display 901 is arranged to show a live view image of the scene captured by the camera 403 and to display any objects or visualisations, for example in as an augmented reality display as will be described in further detail below. The display 901 may be a presence-sensitive display and therefore may comprise the user input unit 906. The presence-sensitive display may include a display component and a presence-sensitive input component. The presence sensitive display may be a touch-screen display arranged to provide a user interface.

The user electronic device 900 may also include a biometric sensor. The biometric sensor may be used to identify a user or users of device based on unique physiological features. The biometric sensor may be: a fingerprint sensor used to capture an image of a user's fingerprint; an iris scanner or a retina scanner configured to capture an image of a user's iris or retina; an ECG module used to measure the user's ECG; or the camera of the user electronic arranged to capture the face of the user. The biometric sensor may be an internal module of the user electronic device. The biometric module may be an external (stand-alone) device which may be coupled to the user electronic device by a wired or wireless link.

User electronic devices in accordance with the present invention are not limited to mobile phones or tablets and may take the form of any electronic device which may be used by a user to perform the methods according to aspects of the present invention. The user electronic device may be a mobile electronic device such as a smartphone, tablet personal computer (PC), mobile phone, smart phone, video telephone, laptop PC, netbook computer, personal digital assistant (PDA), mobile medical device, camera or wearable device. The wearable device may include a head-mounted device such as an Augmented Reality, Virtual Reality or Mixed Reality head-mounted device. The user electronic device may be desktop PC, workstations, television apparatus or a projector, e.g. arranged to project a display onto a surface.

The server 800 may be a single device or may comprise a plurality of distributed devices communicatively coupled to one another, e.g. as a cloud-based server such as cloud server network. The server 800 comprises a electronic module, a storage, and a controller. The controller provides overall control to the server 800. The electronic module 100 transmits and receives various pieces of information required for communication with a user electronic device 900 and/or server 800 under the control of the controller. The server storage stores information for the server 800 such as data identifying garments and user credential information.

In the present embodiment, the wearable article identifier 500 is a primary AR marker 500 located on the inner garment layer 6. In the present embodiment, the primary AR marker 500 is arranged as a layer on the inner face 7 of the first, inner garment layer 6, that is between the first layer 6 and the second, outer garment layers 8. In particular, the primary AR marker 500 is formed over a substantial part of the main body 9 of the garment 200, for example the front portion 20 of the main body 9 of the garment 200.

In an alternative, the primary AR marker 500 can be integrated into the inner garment layer 6.

Figure 20:
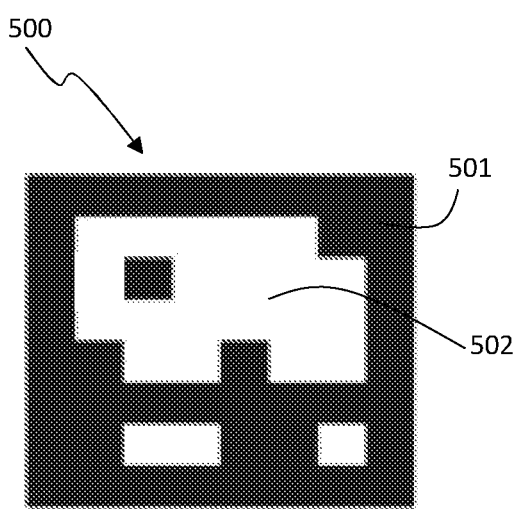
FIG. 20 shows a schematic representation of a wearable article identifier for a wearable article according to aspects of the present disclosure.

The primary AR marker 500 is arranged to have spatially-varying properties, the arrangement of which can be visually represented as a symbol as shown in FIG. 20. The primary marker 500 in this example is derived from the Augmented Reality (AR) marker system known as ARTag.

The primary marker 500 is provided as an arrangement of infrared absorbing regions 501 and infrared non-absorbing regions 502 arranged and configured to encode information therein and which when scanned by infrared radiation emitted by the ToF sensor 902, the infrared radiation is selectively absorbed or reflected to represent a machine-readable code that is readable by the user electronic device 900. In particular, the encoded information in the primary AR marker 500 can be the wearable article identifier.

As such, the primary marker 500 is a non-visible wearable article identifier. The term 'non-visible' refers to the fact that the functionality of the primary marker 500 operates on the non-visible part of the electromagnetic spectrum and in particular in the embodiment described herein, in the infrared part of the spectrum. Whilst the primary marker may be, in some orientations, visible to the human eye, for example due to changes in the reflectivity of the surface of the regions of the primary marker 500 this does make it a visible marker whose image could be captured, for example, by a camera, or seen at long distances.

The primary AR marker 500 may also enable motion tracking to be formed and AR visualisation to be implemented on the user electronic device 900 and displayed to the user.

The primary marker 500 comprises regions of infrared-absorbing 501 and infrared non-absorbing 502 fabric to form an arrangement represented by a visual symbol in the form of a 6×6 grid of black or white cells which represent 36 binary '0' or '1' symbols. The 36-bit sequence encodes a code string and may additionally encode redundant information for error detection, correction and uniqueness over the different rotations of the marker. The black areas 501 represent regions of the primary AR marker 500 which are made from an infrared absorbing fabric, whilst the white areas 502 represent regions made from an infrared non-absorbing fabric, or vice versa.

As mentioned above, the ToF sensor 902 transmits infrared radiation which is selectively absorbed by the infrared-absorbing regions 501 of the primary marker 500 and reflected to the ToF sensor 902 by the non-absorbed infrared signal regions 502, and, as such, the AR primary marker 500 can also be used to identify the garment 200.

Whilst the user electronics device 900 is sensing the electronics module identifier as it is brought into proximity of the electronics module 100, and as described above, the user electronics device 900 is operable to scan primary marker 500 and to store the wearable article identifier encoded in the primary marker 500 in memory 904 along with the associated electronics module identifier, for example in a look-up table. In this way, the wearable article identifier is linked to, and associated with, the electronics module identifier. This enables the identity of the wearer of the garment 200 to be identified as being associated with a particular electronics module 100 for the duration that it is being used by the wearer.

The primary AR marker 500 may also act as a point of reference for the garment 200 and thus enable the position of the garment and the motion of the garment 200 over time to be monitored simply by capturing images of the garment.

Additional secondary AR markers 503 can be provided on the garment 200 at various locations to form anchor points to aid with overlaying AR visualisation, if required.

As an alternative to a primary AR marker, a barcode representation can be used as the primary marker 500. Other identification representation could also be used.

Where a barcode or other non-AR marker is used, then additional secondary AR fiducial markers 503 would be required to anchor visual displays to an image of the wearer. Alternatively, activity and identification information can be displayed to the user without anchoring as will be described in further detail below.

Figure 21:
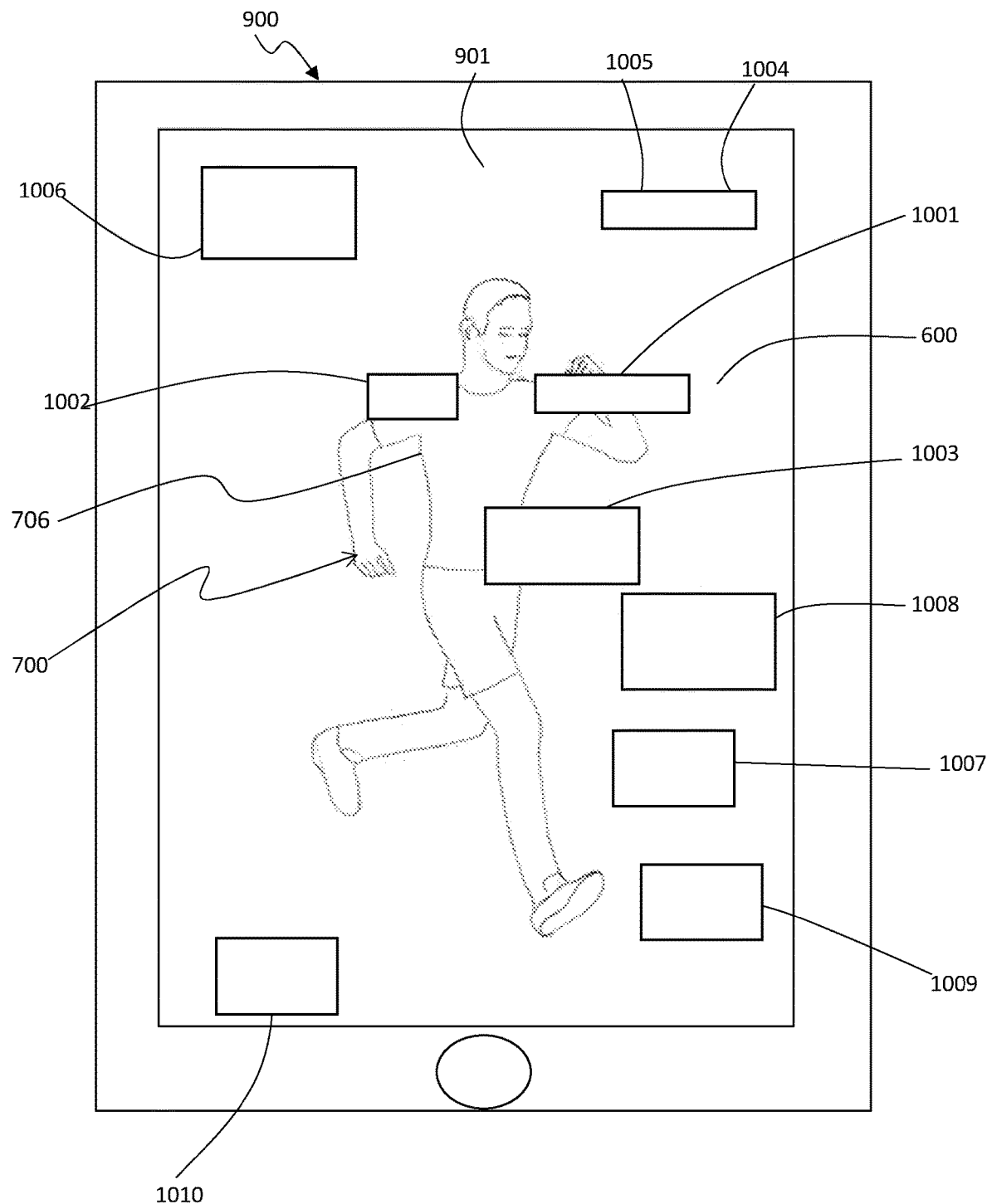
FIG. 21 shows an example interface according to aspects of the present disclosure.

Referring to FIG. 21, there is shown an example user interface 600 displayed on the display 901 of the user electronic device 900. This user interface 600 could also be displayed on the mobile device 300.

The user interface 600 includes a display of a representation 700 of the wearer 706 of the garment 200. The displayed representation 700 of the wearer of the garment 200 is in the form of a live view image which can be a still or a video image as captured by the camera of the user electronic device 900.

The user interface 600 also includes representations of the activity data received by the user electronic device 900. The representation of the activity data in this example is the form of graphical representations or objects that overlay the representation 700 of the wearer 706.

The representation 700 of the activity data can be anchored i.e. displayed at a position determined according to the location of the additional secondary markers 503 on the garment 200. In particular, the additional secondary markers 503 are fiducial markers that acts as a reference position for the garment 200 in relation to the wearer of the garment 200. The position of the representation 706 of the activity data to be displayed is determined using the position of the secondary marker 503 (x1, y1) in the representation 700 of the wearer and a predetermined displacement (x2, y2) from the secondary marker 503 to a feature of interest on the wearer such as the chest region or the arms. In particular, the position of the representation 706 of the activity to be displayed can be determined as (x1, y1)+ (x2, y2). Displays which are arranged as determined by the locations of the secondary markers 503 may include, for example, an ECG trace and heartrate data 1001, core body temperature and skin surface temperature 1002, and blood pressure and blood glucose levels 1003.

The user interface 600 of FIG. 21 can also display activity data for the wearer and other data for the garment 200 at positions which are not determined based on the location of the marker on the garment 200. In this exemplar embodiment, this includes: the signal strength 1004 for the electronic module of the garment 200; the battery level 1005 for a battery of the garment 200; GPS coordinate data 1006; fat level, calories burned, blood lactate level as well as an indication of the type of calories burned 1007; the oxygen level 1008, and sleep tracking, step tracking and hydration level 1009.

The user interface 600 can also displays warnings 1010, indicating, for example when the wearer hydration levels are concerning.

Of course, the user interface 1000 in FIG. 21 is just one example interface and other forms of bio data may be displayed to the user in a different way, for example as shown in FIG. 6.

In an example use case, a sports coach may desire to monitor several players on a team as described above in relation to FIGS. 7 and 8.

As with the first embodiment, there is an initial registration process, for each of the wearable assemblies 10, the electronics module identifier is associated with the wearable article identifier 500. To do this, the user electronics device 900 reads the electronics module identifier and the wearable article identifier 500 for a particular wearer and associates the electronics module identifier to the wearable article identifier as described above.

The user electronics device 900 uses the received electronics module identifier to identify the wearable article identifier 500 associated with the electronics module identifier. In this way, the user electronics device 900 identifies the wearer wearing the respective electronics module 100. The user electronics device 900 may then display the activity data along with identifying information for the wearer on the display 901 using a particular user interface 600, for example as described above, and received from the electronics module 100. The identifying information may include a username, picture or other identifying information.

In some examples, the server 800 receives the activity data from the plurality of electronics modules 900. The user of the user electronics device 900 may desire to view activity data for one or more of the players on the pitch. To do this, the user uses the user electronics device 900 to read the wearable article identifier in the form of the primary AR marker 500 for the player or players. The user electronics device 900 uses the wearable article identifier 500 to identify the electronics module identifier associated with the wearable article identifier 500.

The user electronics device 900 transmits the electronics module identifier to the server 800 as part of a request for activity data. The server 800 transmits the activity data (which may be a processed version of the originally received activity data) for the electronics module identified by the electronics module identifier to the user electronics device 900. The user electronics device 900 may then display the activity data along with identifying information for the wearer. The identifying information may include a username, picture or other identifying information. This approach enables the user electronics device 900 to determine which garment and thus which athlete incoming activity data relates to.

Referring to FIGS. 10 and 11, the method of associating an electronics module 100 with a wearable article for a wearable assembly can be used with the wearable assemblies in this present embodiment described in relation to FIGS. 16 to 21.

Figure 22:
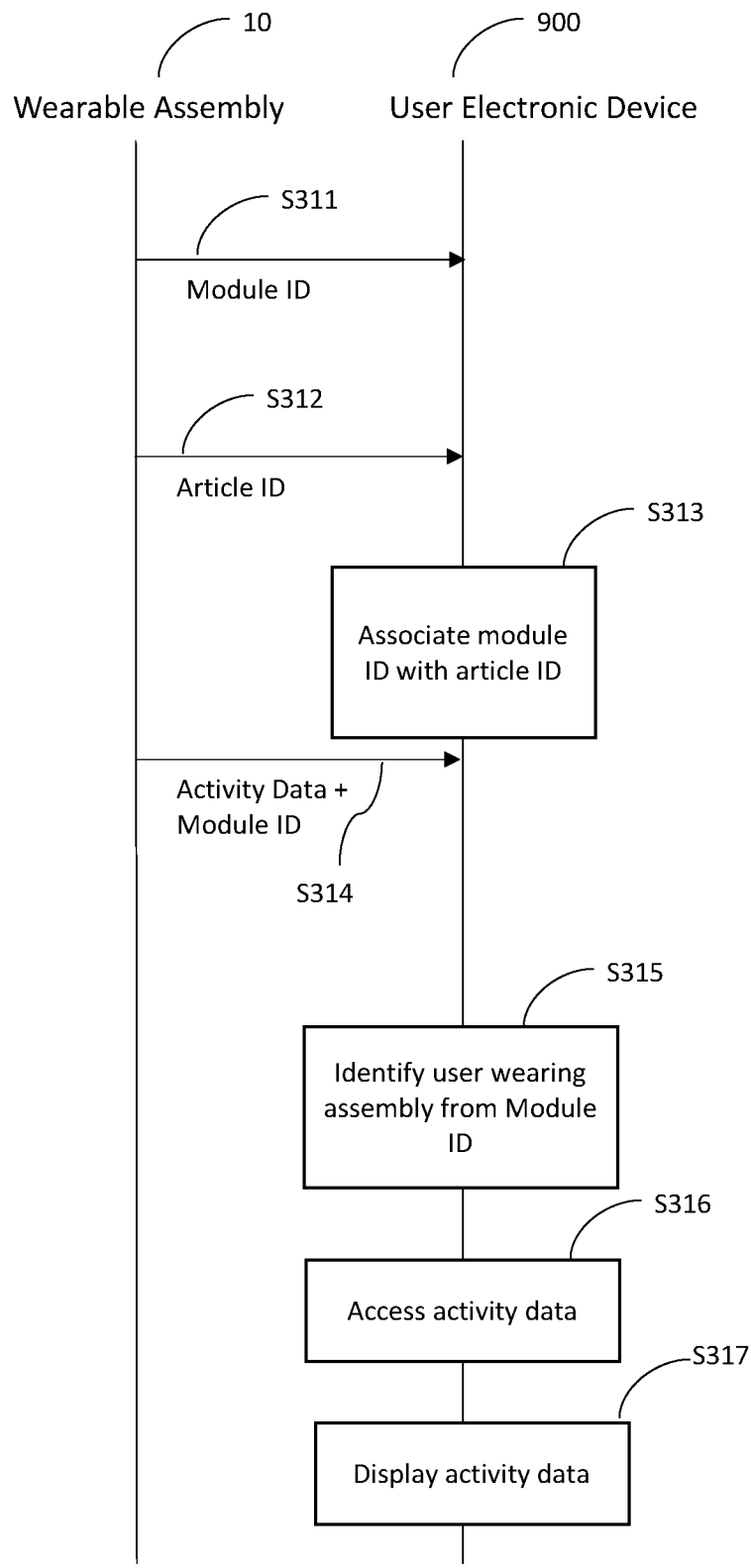
FIG. 22 shows a swim lane diagram for yet another example method according to aspects of the present disclosure.

Referring to FIG. 22, there is shown a swim-lane flow diagram for an example method according to aspects of the present disclosure. The method is performed by a wearable assembly 10 and a user electronics device 900.

In step S311, the user electronics device 900 obtains an electronics module identifier for an electronics module of the wearable assembly 10.

In step S312, the user electronics device 900 obtains a wearable article identifier 500 for a wearable article of the wearable assembly 10.

In step S313, the user electronics device 900 associates the electronics module identifier with the wearable article identifier 500.

In step S314, the electronics module 100 of the wearable assembly 10 transmits activity data and the electronics module identifier to the user electronics device 900. In some examples, the electronics module identifier is not transmitted as this information may be inferred by the user electronics device 900 based on factors such as the properties of the communication and the communication channel used by the electronics module.

In step S315, the user electronics device 900 identifies the wearer wearing the electronics module 100 by identifying the wearable article identifier 500 associated with the electronics module identifier in step S313.

In step S316, the user electronics device 900 accesses the activity data for the identified wearer.

In step S317, the user electronics device 900 displays the activity data for the identified wearer, optionally along with identifying information for the user optionally along with identifying information for the user.

Figure 23:
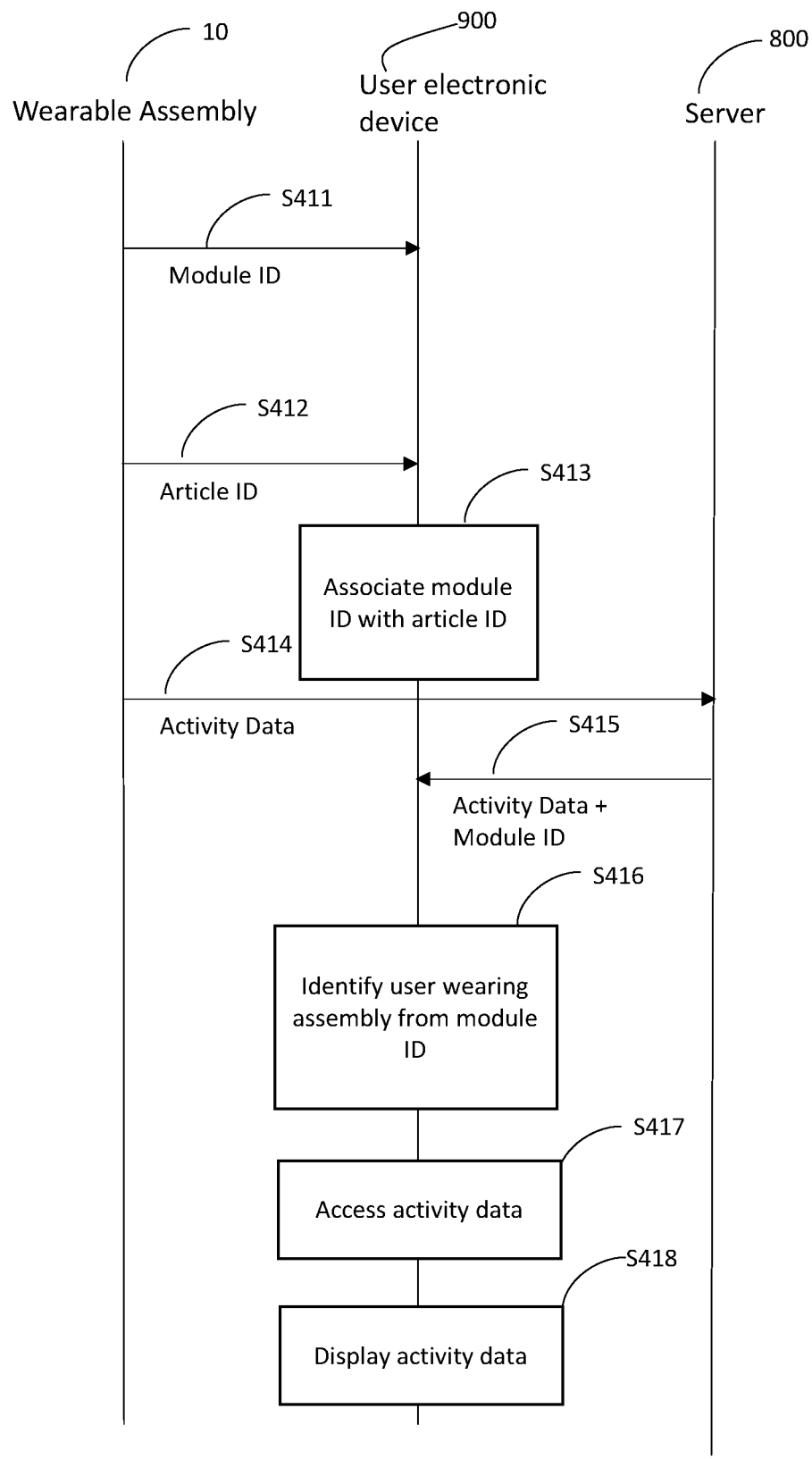
FIG. 23 shows a swim lane diagram for yet another example method according to aspects of the present disclosure.

Referring to FIG. 23, there is shown a swim-lane flow diagram for an example method according to aspects of the present disclosure. The method is performed by a wearable assembly 10, user electronics device 900 and server 800.

In step S411, the user electronics device 900 obtains an electronics module identifier for an electronics module of the wearable assembly 10.

In step S412, the user electronics device 900 obtains a wearable article identifier 500 for a wearable article of the wearable assembly 10.

In step S413, the user electronics device 900 associates the electronics module identifier with the wearable article identifier 500.

In step S414, the electronics module 100 of the wearable assembly 10 transmits activity data and the associated electronics module identifier to the server 800. In some examples, the electronics module identifier is not transmitted as this information may be inferred by the server 800 based on factors such as the properties of the communication and the communication channel used by the electronics module.

In step S415, the server 800 transmits the received activity data and the electronics module identifier to the user electronics device 900.

In step S416, the user electronics device 900 identifies the user wearing the electronics module 100 by identifying the wearable article identifier associated with the electronics module identifier transmitted in step S413.

In step S417, the user electronics device 900 accesses the activity data.

In step S418, the user electronics device 900 displays the accessed activity data, optionally along with identifying information for the user.

Figure 24:
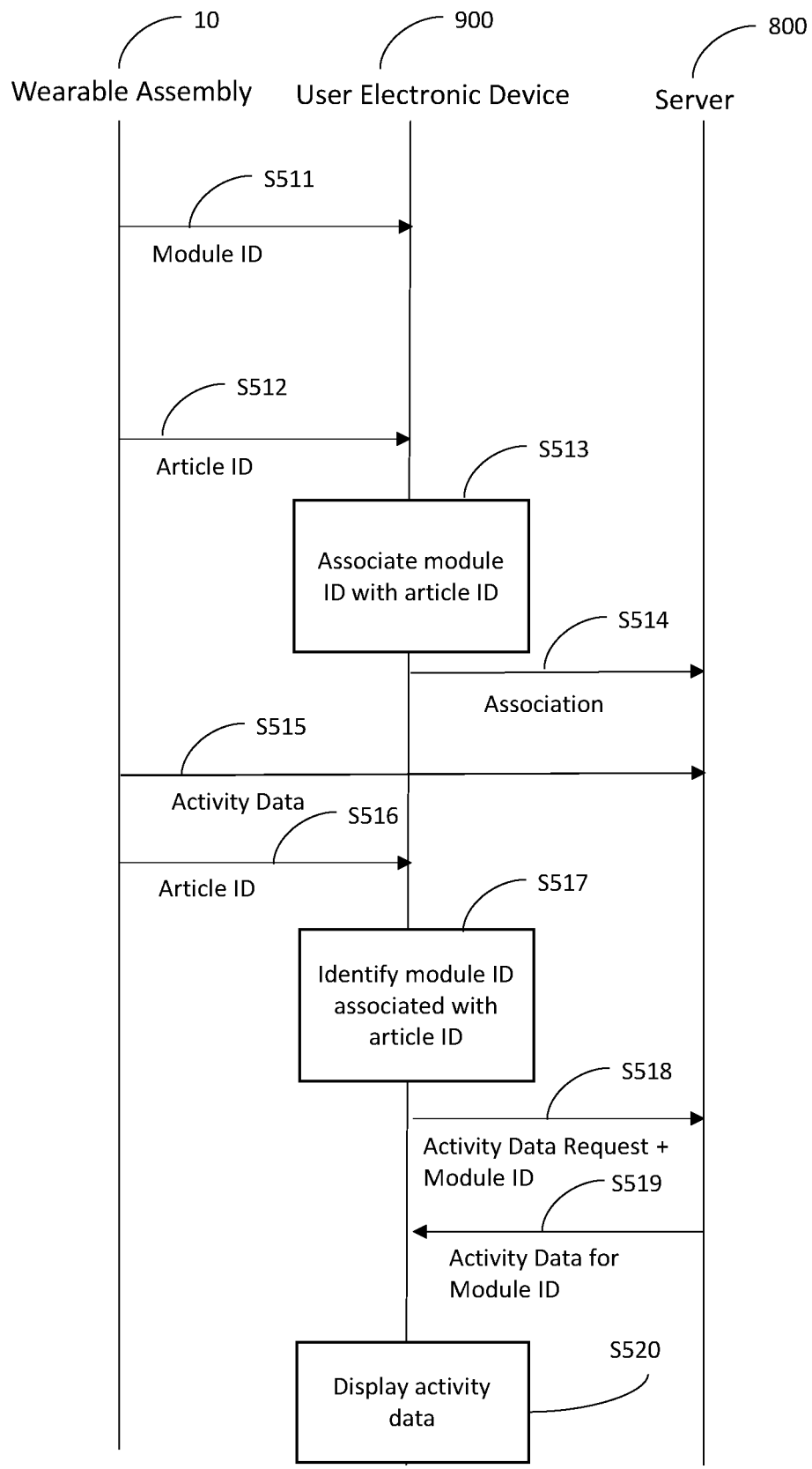
FIG. 24 shows a swim lane diagram for yet another example method according to aspects of the present disclosure.

Referring to FIG. 24, there is shown a swim-lane flow diagram for an example method according to aspects of the present disclosure. The method is performed by a wearable assembly 10, user electronics device 900 and server 800.

In step S511, the user electronics device 900 obtains an electronics module identifier for an electronics module of the wearable assembly 10.

In step S512, the user electronics device 900 obtains a wearable article identifier 500 for a wearable article of the wearable assembly 10.

In step S513, the user electronics device 900 associates the electronics module identifier with the wearable article identifier 500.

In step S514, the user electronics device 900 transmits the association between the electronics module identifier and the wearable article identifier 500 to the server 800.

In step S515, the electronics module 100 of the wearable assembly 100 transmits activity data to the server 800 optionally along with the electronics module identifier.

In step S516, the user electronics device 900 obtains the wearable article identifier 500 from the wearable assembly 10.

In step S517, the user electronics device 900 uses the wearable article identifier 500 to identify an electronics module identifier associated with the wearable article identifier.

In step S518, the user electronics device 900 transmits an activity data request comprising the electronics module identifier to the server 800.

In step S519, the server 800 transmits the received activity data for the relevant electronics module to the user electronics device 900.

In step S520, the user electronics device 900 displays the activity data, optionally along with identifying information for the user.

Figure 25:
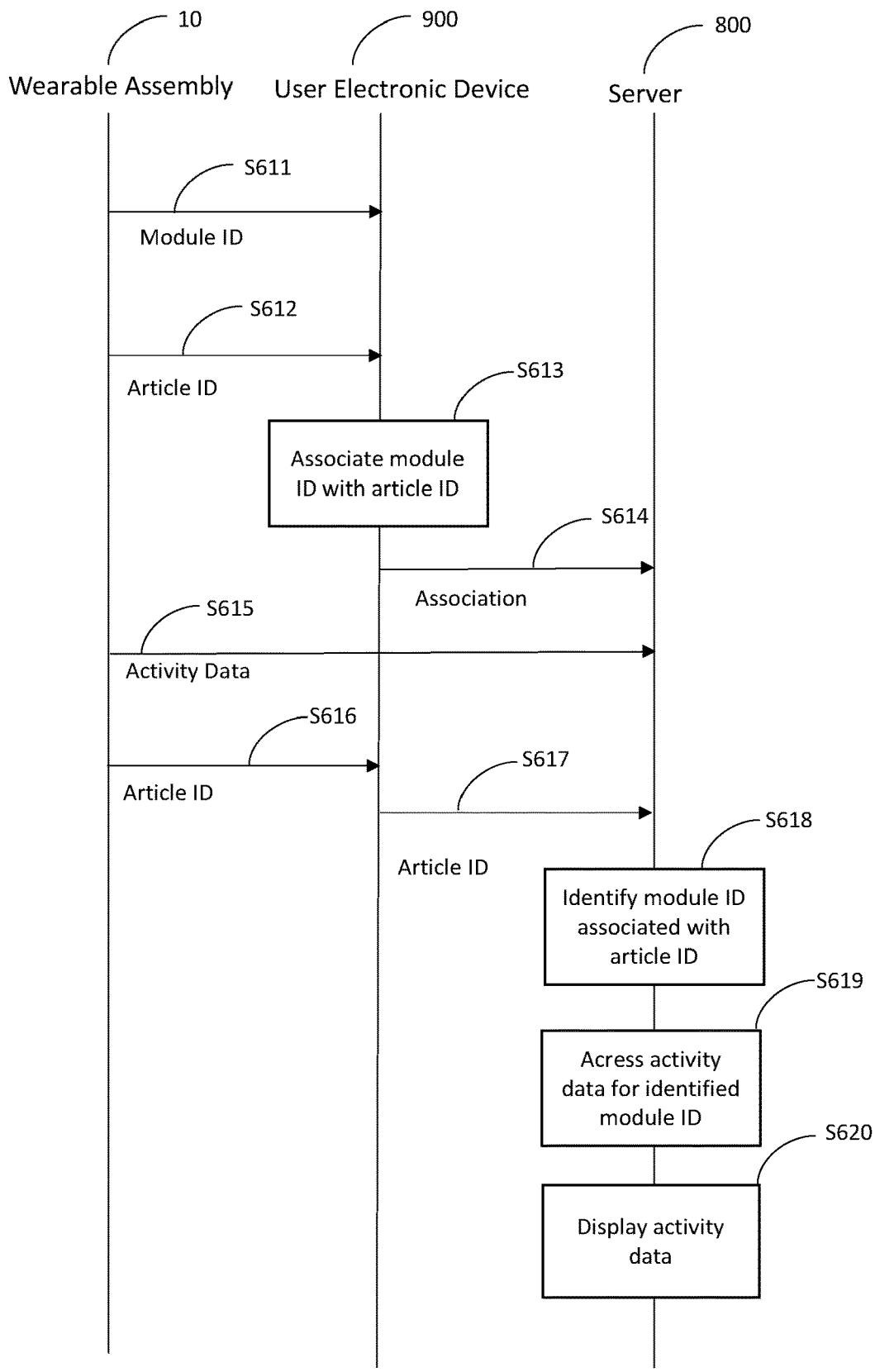
FIG. 25 shows a swim lane diagram for yet another example method according to aspects of the present disclosure.

Referring to FIG. 25, there is shown a swim-lane flow diagram for an example method according to aspects of the present disclosure. The method is performed by a wearable assembly 10, user electronic device 900 and server 800.

In step S611, the user electronics device 900 obtains an electronics module identifier for an electronics module of the wearable assembly 10.

In step S612, the user electronics device 900 obtains a wearable article identifier 500 for a wearable article of the wearable assembly 100.

In step S613, the user electronics device 900 associates the electronics module identifier with the wearable article identifier 500.

In step S614 the user electronics device 900 transmits the association to the server 800. In step S615, the electronics module 100 of the wearable assembly 10 transmits activity data to the server 800 optionally along with the electronics module identifier.

In step S616, the user electronic device 900 obtains a wearable article identifier 500 for the wearable article of the wearable assembly 10.

In step S617, the user electronic device 900 transmits the wearable article identifier 500 to the server 800.

In step S618, the server 800 uses the wearable article identifier to identify an electronics module identifier for an electronics module associated with the wearable article identifier 500.

In step S619, the server 800 uses the electronics module identifier to obtain activity data for the user wearing the wearable article.

In step S620, the server 800 displays the activity data, optionally along with identifying information for the user.

The primary marker 500 can be formed using a layer of an infrared absorbing material and forming the primary marker 500 using a suitable transfer method. Alternatively, to form the primary marker 500 integrally with the inner layer 6 or outer layer 8 of the main body portion 9 of the garment 200 an infrared absorbing yarn could be used.

While the particular examples mentioned above refer to wearable articles in the form of garments, it will be appreciated that the present disclosure is not limited to such examples and other forms of wearable article are within the scope of the present disclosure. The wearable article may be, for example, any form of electronic device which may be worn by a user such as a smart watch, necklace, bracelet, or glasses. The wearable article may be a textile article.

While the examples mentioned above refer to non-visible symbols operating in the infrared part of the electromagnetic spectrum, other regions of the electromagnetic spectrum could be utilised.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method comprising:
reading an electronics module identifier for an electronics module;
reading a wearable article identifier for a wearable article associated with the electronics module; and
associating the electronics module identifier with the wearable article identifier,
obtaining activity data and the electronics module identifier from the electronics module, and
identifying the user wearing the electronics module by identifying the wearable article identifier associated with the electronics module identifier,
wherein the activity data represents biosignals measured by sensing components of the wearable article.

2. The method according to claim 1, wherein reading the electronics module identifier comprises communicating with the electronics module.

3. The method according to claim 2, wherein the communication is over a wireless communication protocol.

4. The method according to claim 3, wherein reading the electronics module identifier comprises triggering the electronics module to transmit the electronics module identifier over the wireless communication protocol.

5. The method according to claim 1, wherein reading the wearable article identifier comprises reading a machine-readable code of the wearable article.

6. The method according to claim 5, wherein reading the machine-readable code comprises capturing an image of the machine-readable code.

7. The method according to claim 1, further comprising: displaying the activity data along with identifying information for the user.

8. The method according to claim 1, further comprising: obtaining activity data and electronics module identifiers from a plurality of electronics modules; and
for at least one of the electronics modules, identifying the user wearing the electronics module by identifying the wearable article identifier associated with the received electronics module identifier for the wearable article.

9. The method according to claim 8, further comprising, for a plurality of the electronic modules, identifying the user wearing the electronics module by identifying the wearable article identifier associated with the received electronics module identifier for the wearable article.

10. The method according to claim 9, further comprising displaying the activity data for the plurality of electronics modules along with identifying information for the users associated with the plurality of electronics modules.

11. The method according to claim 1, further comprising:
obtaining the wearable article identifier for the wearable article;
using the wearable article identifier to identify the electronics module identifier associated with the wearable article identifier; and
using the electronics module identifier to obtain activity data from for the user wearing the wearable article from the electronics module.

12. The method according to claim 11, further comprising:
displaying the activity data along with identifying information for the user.

13. The method according to claim 11, further comprising:
obtaining wearable article identifiers for a plurality of wearable articles;
for at least one of the wearable article identifiers:
(a) identifying an electronics module identifier associated with the wearable article identifier; and
(b) using the electronics module identifier to obtain activity data for the user wearing the wearable article from the electronics module.

14. The method according to claim 12, further comprising:
obtaining wearable article identifiers for a plurality of wearable articles;
for at least one of the wearable article identifiers:
(a) identifying an electronics module identifier associated with the wearable article identifier; and
(b) using the electronics module identifier to obtain activity data for the user wearing the wearable article from the electronics module.

15. The method according to claim 13, further comprising, for a plurality of the wearable article identifiers: identifying an electronics module identifier associated with the wearable article identifier; and using the electronics module identifier to obtain activity data from for the user wearing the wearable article from the electronics module.

16. The method according to claim 15, further comprising displaying the activity data for the plurality of electronic modules along with identifying information for the users associated with the plurality of electronic modules.

17. The method according to claim 11, wherein using the identified electronics module identifier to obtain activity data from the electronics module comprises: receiving activity data and an electronics module identifier from an electronics module; and determining that the received electronics module identifier matches the identified electronics module identifier.

18. The method according to claim 17, wherein the activity data and the electronics module identifier are received indirectly from the electronics module via an external apparatus.

19. The method according to claim 11, wherein using the electronics module identifier to obtain activity data from for the user wearing the wearable article from the electronics module comprises transmitting the electronics module identifier to an external apparatus and receiving, from the external apparatus, activity data from the electronics module.

20. The method according to claim 1, further comprising transmitting the associated electronics module identifier and the wearable article identifier to an external apparatus.

21. The method according to claim 1, wherein the step of reading a wearable article identifier for a wearable article comprises reading a non-visible wearable article identifier for a wearable article associated with the electronics module; and the step of associating the electronics module identifier with the wearable article identifier comprises associating the electronics module identifier with the non-visible wearable article identifier.

22. The method according to claim 1, wherein the sensing components measure one or a combination of bioelectrical, bioimpedance, biochemical, biomechanical, bioacoustics, biooptical, or biothermal signals of the user.

* * * * *